(12) United States Patent
Berg et al.

(10) Patent No.: US 6,479,497 B1
(45) Date of Patent: Nov. 12, 2002

(54) SUBSTITUTED CHROMAN DERIVATIVES

(75) Inventors: Stefan Berg, Ekerö; Martin Nylöf; Svante Ross, both of Södertälje; Seth-Olov Thorberg, Strängnäs, all of (SE)

(73) Assignee: Astrazeneca AB (SE)

( * ) Notice: Subject to any disclaimer, the term of this patent is extended or adjusted under 35 U.S.C. 154(b) by 0 days.

(21) Appl. No.: 09/171,570

(22) PCT Filed: Sep. 9, 1998

(86) PCT No.: PCT/SE98/01603

§ 371 (c)(1),
(2), (4) Date: Oct. 21, 1998

(87) PCT Pub. No.: WO99/14212

PCT Pub. Date: Mar. 25, 1999

(30) Foreign Application Priority Data

Sep. 18, 1997 (SE) ................................. 9703377

(51) Int. Cl.[7] .................... A61K 31/496; C07D 405/06; C07D 405/14
(52) U.S. Cl. .................. 514/254.11; 544/376; 544/358; 514/225.05
(58) Field of Search ................................. 514/247, 252, 514/253, 254.11, 255.05; 544/336, 358, 359, 362, 376

(56) References Cited

U.S. PATENT DOCUMENTS

| 4,631,282 A | * 12/1986 | Cassidy et al. | 514/254 |
| 5,420,151 A | 5/1995 | Hammarberg et al. | 514/456 |
| 6,040,308 A | * 3/2000 | Hausler et al. | 514/253 |

FOREIGN PATENT DOCUMENTS

| WO | 9012795 | 11/1990 |
| WO | 9109853 | 7/1991 |
| WO | 9707120 | 2/1997 |

* cited by examiner

*Primary Examiner*—Alan L. Rotman
*Assistant Examiner*—Rita Desai

(57) ABSTRACT

The present invention relates to new new piperidyl or piperazinyl-substituted dihydro-2H-1-benzopyran derivatives compound having the formula (I)

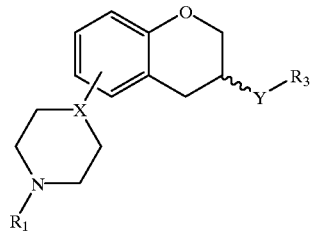

(I)

wherein
X is N or CH;
Y is $NR_2CH_2$, $CH_2NR_2$, $NR_2CO$, $CONR_2$, $NR_2SO_2$ or $NR_2CONR_2$ wherein $R_2$ is H or $C_1$–$C_6$ alkyl;
$R_1$ is H, $C_1$–$C_6$ alkyl or $C_3$–$C_6$ cycloalkyl;
$R_3$ is $C_1$–$C_6$ alkyl, $C_3$–$C_6$ cycloalkyl or $(CH_2)_n$-aryl, wherein aryl is phenyl or a heteroaromatic ring containing one or two heteroatoms selected from N, O and S and which may be mono- or di-substituted with $R_4$ and/or $R_5$;
and n is 0–4;
as (R)-enantiomers, (S)-enantiomers or a racemate in the form of a free base or a pharmaceutically acceptable salt or solvate thereof, a process for their preparation, pharmaceutical compositions containing said therapeutically active compounds and to the use of said active compounds.

11 Claims, 1 Drawing Sheet

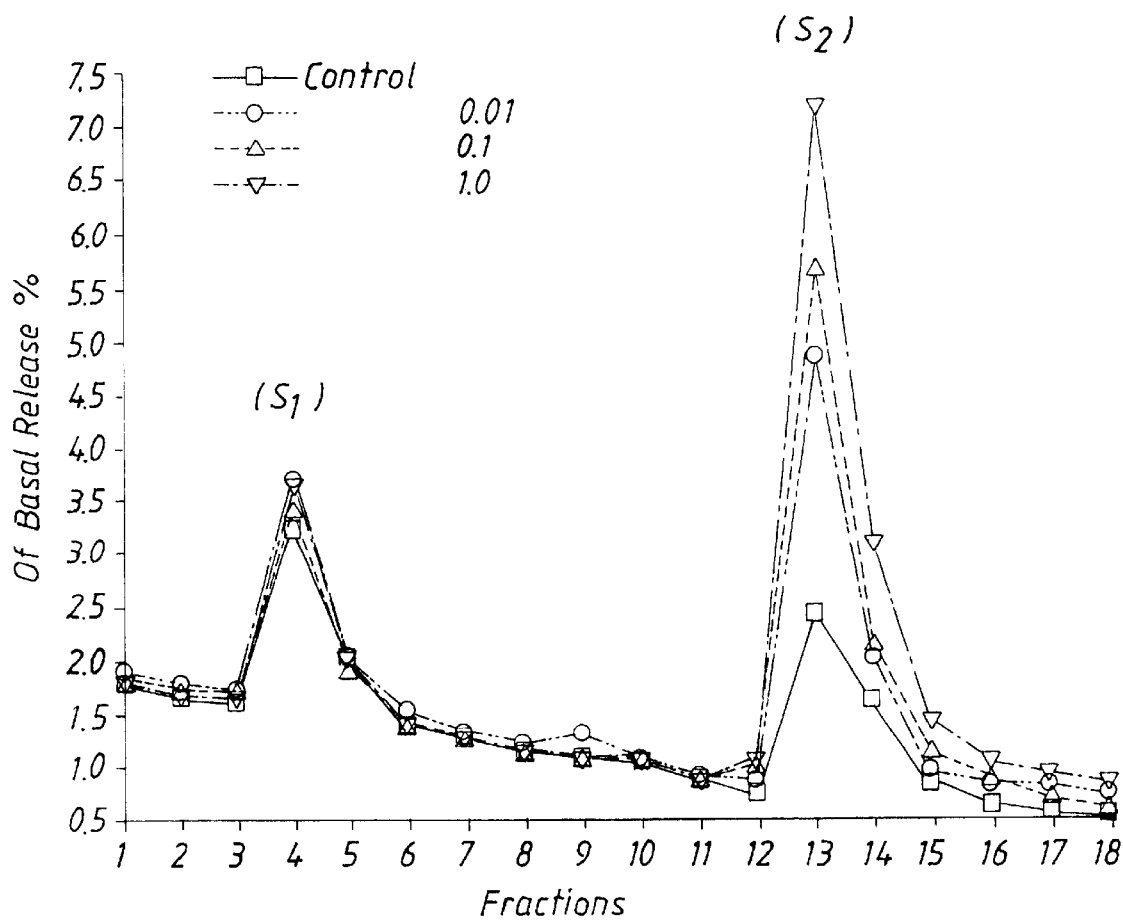

SUBSTITUTED CHROMAN DERIVATIVES

This application is the National Stage of International Application Number PCT/SE98/01603, filed Sep. 9, 1998.

FIELD OF THE INVENTION

The present invention relates to new piperidyl- or piperazinyl-substituted dihydro-2H-1-benzopyran derivatives as (R)-enantiomers, (S)-enantiomers or racemates in the form of free base or pharmaceutically acceptable salts or solvates thereof, a process for their preparation, pharmaceutical compositions containing said therapeutically active compounds and to the use of said active compounds in therapy.

An object of the invention is to provide compounds for therapeutic use, especially compounds having a selective effect at a subgroup of 5-hydroxytryptamine receptors, designated the h5-$HT_{1B}$-receptor (previously called the 5-$HT_{1D_\beta}$-receptor) in mammals including man.

It is also an object of the invention to provide compounds with a therapeutic effect after oral administration.

BACKGROUND OF THE INVENTION

Various central nervous system disorders such as depression, anxiety, etc. appear to involve the disturbance of the neurotransmitters noradrenaline (NA) and 5-hydroxytryptamine (5-HT), the latter also known as serotonin. The drugs most frequently used in the treatment of depression are believed to act by improving the neurotransmission of either or both of these physiological agonists. It appears that the enhancement of 5-HT neurotransmission primarily affects the depressed mood and anxiety, whereas the enhancement of noradrenaline neurotransmission affects the retardation symptoms occurring in depressed patients. The invention concerns compounds which have an effect on 5-HT neurotransmission.

Serotonin, or 5-HT, activity is believed to be involved in many different types of psychiatric disorders. For instance it is believed that an increase in 5-HT activity is associated with anxiety, while a decrease in 5-HT release has been associated with depression. Serotonin has in addition been implicated in such diverse conditions as eating disorders, gastrointestinal disorders, cardiovascular regulation disorders and sexual disturbances.

The 5-HT Receptors

The various effects of 5-HT may be related to the fact that serotoninergic neurons stimulate the secretion of several hormones, e.g. cortisol, prolactin, β-endorphin, vasopressin and others. The secretion of each of these other hormones appears to be regulated on a specific basis by several different 5-HT (serotonin) receptor subtypes. With the aid of molecular biology techniques, to date these receptors have been classified as 5-$HT_1$, 5-$HT_2$, 5-$HT_3$, 5-$HT_4$, 5-$HT_5$, 5-$HT_6$ and 5-$HT_7$ with the 5-$HT_1$ receptor further divided into the 5-$HT_{1A}$, 5-$HT_{1B}$, 5-$HT_{1D}$, 5-$HT_{1E}$ and 5-$HT^{1F}$ subtypes. Each receptor subtype is involved in a different serotonin function and has different properties.

Regulation of the 5-HT Transmission

The release of 5-HT is feedback-regulated by two different subtypes of 5-HT receptors. Inhibitory 5-$HT_{1A}$ autoreceptors are located on the cell bodies in the raphé nuclei which upon stimulation by 5-HT decrease the impulse propagation in the 5-HT neurons and thereby reduce the 5-HT released at the nerve terminals. Another subtype of inhibitory 5-HT receptors is located on the 5-HT nerve terminals, the h5-$HT_{1B}$ receptors (in rodents the r5-$HT_{1B}$ receptors) which regulate the synaptic concentration of 5-HT by controlling the amount of 5-HT that is released. An antagonist of these terminal autoreceptors thus increases the amount of 5-HT released by nerve impulses which has been shown in both in vitro and in vivo experiments.

The use of an antagonist of the terminal h5-$HT_{1B}$ autoreceptor will accordingly increase the synaptic 5-HT concentration and enhance the transmission in the 5-HT system. It would thus produce an antidepressant effect making it useful as a medication for depression. Other localizations of h5-$HT_{1B}$ receptor subtype also exist. A large part of these postsynaptic receptors appear to be located on nerve terminals of other neuronal systems (so called heteroreceptors). Since the h5-$HT_{1B}$ receptor mediates inhibitory responses an antagonist of this receptor subtype might also increase the release of other neurotransmitters than 5-HT.

Compounds having h5-$HT_{1B}$ activity may according to well known and recognised pharmacological tests be divided into full agonists, partial agonists and antagonists.

DISCLOSURE OF THE INVENTION

The object of the present invention is to provide compounds having a selective effect at the h5-$HT_{1B}$ receptor, preferably antagonistic properties, as well as having a good bioavailability. The effect on the other receptors chosen from, for example, the 5-$HT_{1A}$, 5-$HT_{2A}$, $D_1$, $D_{2A}$, $D_3$, $\alpha_1$ and $\alpha_2$ receptor has been investigated.

Accordingly, the present invention provides compounds of the formula I

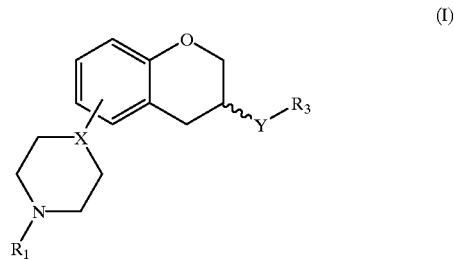

(I)

wherein

X is N or CH;

Y is $NR_2CH_2$, $CH_2-NR_2$, $NR_2-CO$, $CO-NR_2$, $NR_2SO_2$ or $NR_2CONR_2$ wherein $R_2$ is H or $C_1-C_6$ alkyl;

$R_1$ is H, $C_1-C_6$ alkyl or $C_3-C_6$ cycloalkyl;

$R_3$ is $C_1-C_6$ alkyl, $C_3-C_6$ cycloalkyl or $(CH_2)_n$-aryl,
wherein aryl is phenyl or a heteroaromatic ring containing one or two heteroatoms selected from N, O and S and which may be mono- or di-substituted with $R_4$ and/or $R_5$;
wherein $R_4$ is H, $C_1-C_6$ alkyl, $C_3-C_6$ cycloalkyl, halogen, CN, $CF_3$, OH, $C_1-C_6$ alkoxy, $NR_6R_7$, $OCF_3$, $SO_3CH_3$, $SO_3CF_3$, $SO_2NR_6R_7$, phenyl phenyl-$C_1-C_6$ alkyl, phenoxy, $C_1-C_6$ alkylphenyl, an optionally substituted heterocyclic ring containing one or two heteroatoms selected from N, O, S, SO and $SO_2$ wherein the substituent(s) is (are) selected from $C_1-C_6$ alkyl, $C_3-C_6$ cycloalkyl phenyl-$C_1-C_6$ alkyl, $(CH_2)_mOR_9$ wherein m is 2–6 and $R_9$ is H, $C_1-C_6$ alkyl, $C_3-C_6$ cycloalkyl or phenyl-$C_1-C_6$ alkyl, and $COR_8$, an optionally substituted heteroaromatic ring containing one or two heteroatoms selected from N, O and S wherein the substituent(s) is (are) selected from $C_1$–$C_6$ alkyl, $C_3$–$C_6$ cycloalkyl and phenyl-$C_1$–$C_6$ alkyl, or $COR_8$;
  wherein $R_6$ is H, $C_1$–$C_6$ alkyl or $C_3$–$C_6$ cycloalkyl;
  $R_7$ is H, $C_1$–$C_6$ alkyl or $C_3$–$C_6$ cycloalkyl; and
  $R_8$ is $C_1$–$C_6$ alkyl, $C_3$–$C_6$ cycloalkyl $CF_3$, $NR_6R_7$, phenyl, a heteroaromatic ring containing one or two heteroatoms selected from N, O and S or a heterocyclic ring containing one or two heteroatoms selected from N, O, S, SO and $SO_2$;
  $R_5$ is H, OH, $CF_3$, $OCF_3$, halogen, $C_1$–$C_6$ alkyl or $C_1$–$C_6$ alkoxy;
  and n is 0–4;
as (R)-enantiomers, (S)-enantiomers or a racemate in the form of a free base or a pharmnaceutically acceptable salt or solvate thereof which possess a high selective effect at the h5-$HT_{1B}$ receptor and also show sufficient bioavailability after oral administration.

In the present context $C_1$–$C_6$ alkyl may be straight or branched. $C_1$–$C_6$ alkyl may be methyl, ethyl, n-propyl, i-propyl, n-butyl, i-butyl, s-butyl, t-butyl, n-pentyl, i-pentyl, t-pentyl, neo-pentyl, n-hexyl or i-hexyl In the present context $C_1$–$C_6$ alkoxy may be straight or branched. $C_1$–$C_6$ alkoxy may be methoxy, ethoxy, n-propoxy, i-propoxy, n-butoxy, i-butoxy, s-butoxy, t-butoxy, n-pentyloxy, i-pentyloxy, t-pentyloxy, neo-pentyloxy, n-hexyloxy or i-hexyloxy.

In the present context $C_3$–$C_6$ cycloalkyl may be cyclopropyl, cyclobutyl, cyclopentyl or cyclohexyl, preferably cyclohexyl.

In the present context halogen may be fluoro, chloro, bromo or iodo.

In the present context the heteroaromatic ring containing one or two heteroatoms selected from N, O and S preferably is a 5- or 6-membered heteroaromatic ring and may be furyl, imidazolyl, isoxazolyl, isothiazolyl, oxazolyl, pyrazinyl, pyrazolyl, pyridazinyl, pyridyl, pyrimidyl, pyrrolyl, thiazolyl or thienyl. The heteroaromatic ring can be either substituted or unsubstituted.

In the present context the heterocyclic ring containing one or two heteroatoms selected from N, O, S, SO and $SO_2$ may optionally contain a carbonyl function and is preferably a 5-, 6- or 7-membered heterocyclic ring and may be imidazolidinyl, imidazolinyl, morpholinyl, piperazinyl, piperidyl, piperidonyl, pyrazolidinyl, pyrazolinyl, pyrrolidinyl, pyrrolinyl, tetrahydropyranyl, thiomorpholinyl, preferably piperidimo, 1-piperazinyl, morpholino, thiomorpholino and 4-piperidon-1-yl.

A preferred embodiment of the invention relates to compounds of formula I wherein Y is NHCO or CONH i.e. amides. Of these compounds, the compounds wherein $R_3$ is unsubstituted phenyl, or mono- or di-substituted phenyl, and especially ortho-, meta- or para-substituted phenyl, and particularly these wherein the substituent $R_4$ is phenyl, phenyl-$C_1$–$C_6$ alkyl, cyclohexyl, piperidino, 1-piperazinyl, morpholino, $CF_3$, 4-piperidon-1-yl, n-butoxy or $COR_8$ wherein $R_8$ is phenyl, cyclohexyl, 4-piperidon-1-yl, 1-piperazinyl, morpholino, $CF_3$, piperidino or $NR_6R_7$, are preferred.

Examples of combinations of substituents are:

X is N, Y is $CONR_2$, $R_1$ is H, $CH_3$, $C_2H_5$ or $C_3H_7$, $R_2$ is H, $R_3$ is $(CH_2)_2$-phenyl, $R_4$ is piperidino, $R_5$ is H;

X is N, Y is $NR_2CO$, $R_1$ is H, $CH_3$, $C_2H_5$ or $C_3H_7$, $R_2$ is H, $R_3$ is $(CH_2)_2$-phenyl, $R_4$ is phenyl, phenylmethyl or phenylethyl, $R_5$ is H;

X is N, Y is $NR_2CO$, $R_1$ is H, $CH_3$, $C_2H_5$ or $C_3H_7$, $R_2$ is H, $R_3$ is phenyl, $R_4$ is piperidino, $R_5$ is H;

X is N, Y is $CONR_2$, $R_1$ is H, $CH_3$, $C_2H_5$ or $C_3H_7$, $R_2$ is H, $R_3$ is phenyl, $R_4$ is hydroxyethyl-piperazinyl, $R_5$ is H;

X is CH, Y is $CONR_2$, $R_1$ is H, $CH_3$, $C_2H_5$ or $C_3H_7$, $R_2$ is H, $R_3$ is $CH_2$-phenyl, $R_4$ is phenyl, phenylmethyl or phenylethyl, $R_5$ is H;

X is CH, Y is $NR_2CO$, $R_1$ is H, $CH_3$, $C_2H_5$ or $C_3H_7$, $R_2$ is H, $R_3$ is phenyl, $R_4$ is piperidino, $R_5$ is H;

X is N, Y is $NR_2CO$, $R_1$ is H, $CH_3$, $C_2H_5$ or $C_3H_7$, $R_2$ is H, $R_3$ is $(CH_2)_2$-phenyl;

X is CH, Y is $CONR_2$, $R_1$ is H, $CH_3$, $C_2H_5$ or $C_3H_7$, $R_2$ is H, $R_3$ is $CH_2$-phenyl;

X is N, Y is $NR_2CO$, $R_1$ is H, $CH_3$, $C_2H_5$ or $C_3H_7$, $R_2$ is H, $R_3$ is $CH_2$-phenyl; phenyl, phenylmethyl or phenylethyl, $R_5$ is H;

X is CH, Y is $NR_2CO$, $R_1$ is H, $CH_3$, $C_2H_5$ or $C_3H_7$, $R_2$ is H, $R_3$ is phenyl, $R_4$ is morpholino, $R_5$ is H;

X is CH, Y is $CONR_2$, $R_1$ is H, $CH_3$, $C_2H_5$ or $C_3H_7$, $R_2$ is H, $R_3$ is phenyl, $R_4$ is morpholino, $R_5$ is H;

X is CH, Y is $CONR_2$, $R_1$ is H, $CH_3$, $C_2H_5$ or $C_3H_7$, $R_2$ is H, $R_3$ is phenyl, $R_4$ is piperidino, $R_5$ is H;

X is N, Y is $CONR_2$, $R_1$ is H, $CH_3$, $C_2H_5$ or $C_3H_7$, $R_2$ is H, $R_3$ is $CH_2$-phenyl, $R_4$ is morpholino, $R_5$ is H;

X is N, Y is $NR_2CO$, $R_1$ is H, $CH_3$, $C_2H_5$ or $C_3H_7$, $R_2$ is H, $R_3$ is $CH_2$-phenyl, $R_4$ is morpholino, $R_5$ is H;

X is CH, Y is $NR_2CO$, $R_1$ is H, $CH_3$, $C_2H_5$ or $C_3H_7$, $R_2$ is H, $R_3$ is $(CH_2)_2$-phenyl, $R_4$ is piperidino,.$R_5$ is H;

X is N, Y is $NR_2CO$, $R_1$ is H, $CH_3$, $C_2H_5$ or $C_3H_7$, $R_2$ is H, $R_3$ is phenyl, $R_4$ is hydroxyethyl-piperazinyl, $R_5$ is H;

X is CH, Y is $CONR_2$, $R_1$ is H, $CH_3$, $C_2H_5$ or $C_3H_7$, $R_2$ is H, $R_3$ is phenyl;

X is N, Y is $CONR_2$, $R_1$ is H, $CH_3$, $C_2H_5$ or $C_3H_7$, $R_2$ is H, $R_3$ is phenyl, $R_4$ is morpholino, $R_5$ is H;

X is N, Y is $CONR_2$, $R_1$ is H, $CH_3$, $C_2H_5$ or $C_3H_7$, $R_2$ is H, $R_3$ is phenyl, $R_4$ is piperidino, $R_5$ is H;

X is N, Y is $NR_2CO$, $R_1$ is H, $CH_3$, $C_2H_5$ or $C_3H_7$, $R_2$ is H, $R_3$ is phenyl, $R_4$ is benzyloxyethyl-piperazinyl, $R_5$ is H;

X is CH, Y is $NR_2CO$, $R_1$ is H, $CH_3$, $C_2H_5$ or $C_3H_7$, $R_2$ is H, $R_3$ is $(CH_2)$-phenyl;

X is CH, Y is $NR_2CO$, $R_1$ is H, $CH_3$, $C_2H_5$ or $C_3H_7$, $R_2$ is H, $R_3$ is phenyl, $R_4$ is phenyl, phenylmethyl or phenylethyl, $R_5$ is H;

X is N, Y is $CONR_2$, $R_1$ is H, $CH_3$, $C_2H_5$ or $C_3H_7$, $R_2$ is H, $R_3$ is $(CH_2)_2$-phenyl;

X is N, Y is $CONR_2$, $R_1$ is H, $CH_3$, $C_2H_5$ or $C_3H_7$, $R_2$ is H, $R_3$ is $CH_2$-phenyl, $R_4$ is piperidino, $R_5$ is H;

X is N, Y is $NR_2CO$, $R_1$ is H, $CH_3$, $C_2H_5$ or $C_3H_7$, $R_2$ is H, $R_3$ is $(CH_2)_2$-phenyl, $R_4$ is piperidino, $R_5$ is H;

X is N, Y is $CONR_2$, $R_1$ is H, $CH_3$, $C_2H_5$ or $C_3H_7$, $R_2$ is H, $R_3$ is phenyl, $R_4$ is phenyl, phenylmethyl or phenylethyl, $R_5$ is H;

X is N, Y is $NR_2CO$, $R_1$ is H, $CH_3$, $C_2H_5$ or $C_3H_7$, $R_2$ is H, $R_3$ is phenyl, $R_4$ is morpholino, $R_5$ is H;

X is CH, Y is $CONR_2$, $R_1$ is H, $CH_3$, $C_2H_5$ or $C_3H_7$, $R_2$ is H, $R_3$ is $CH_2$-phenyl, $R_4$ is piperidino, $R_5$ is H;

X is N, Y is $CONR_2$, $R_1$ is H, $CH_3$, $C_2H_5$ or $C_3H_7$, $R_2$ is H, $R_3$ is $CH_2$-phenyl;

X is N, Y is $CONR_2$, $R_1$ is H, $CH_3$, $C_2H_5$ or $C_3H_7$, $R_2$ is H, $R_3$ is $(CH_2)_2$-phenyl, $R_4$ is morpholino, $R_5$ is H;

X is N, Y is $CONR_2$, $R_1$ is H, $CH_3$, $C_2H_5$ or $C_3H_7$, $R_2$ is H, $R_3$ is phenyl, $R_4$ is benzyloxyethyl-piperazinyl, $R_5$ is H;

X is N, Y is $CONR_2$, $R_1$ is H, $CH_3$, $C_2H_5$ or $C_3H_7$, $R_2$ is H, $R_3$ is phenyl, $R_4$ is $COR_8$, $R_8$ is morpholino;

X is CH, Y is $NR_2CO$, $R_1$ is H, $CH_3$, $C_2H_5$ or $C_3H_7$, $R_2$ is H, $R_3$ is $CH_2$-phenyl, $R_4$ is phenyl, phenylmethyl or phenylethyl, $R_5$ is H;

X is CH, Y is $NR_2CO$, $R_1$ is H, $CH_3$, $C_2H_5$ or $C_3H_7$, $R_2$ is H, $R_3$ is $(CH_2)_2$-phenyl, $R_4$ is morpholino, $R_5$ is H;

X is N, Y is $CONR_2$, $R_1$ is H, $CH_3$, $C_2H_5$ or $C_3H_7$, $R_2$ is H, $R_3$ is $(CH_2)_2$-phenyl, $R_4$ is phenyl, phenylmethyl or phenylethyl, $R_5$ is H;

X is N, Y is $NR_2CO$, $R_1$ is H, $CH_3$, $C_2H_5$ or $C_3H_7$, $R_2$ is H, $R_3$ is phenyl, $R_4$ is phenyl, phenylmethyl or phenylethyl, $R_5$ is H;

X is CH, Y is $NR_2CO$, $R_1$ is H, $CH_3$, $C_2H_5$ or $C_3H_7$, $R_2$ is H, $R_3$ is $CH_2$-phenyl, $R_4$ is phenyl, piperidino, $R_5$ is H;

X is CH, Y is $NR_2CO$, $R_1$ is H, $CH_3$, $C_2H_5$ or $C_3H_7$, $R_2$ is H, $R_3$ is $CH_2$-phenyl, $R_4$ is $COR_8$, $R_8$ is $NR_6R_7$, $R_6R_7CH_3$, $C_2H_5$ or $C_3H_7$;

X is CH, Y is $CONR_2$, $R_1$ is H, $CH_3$, $C_2H_5$ or $C_3H_7$, $R_2$ is H, $R_3$ is phenyl, $R_4$ is phenyl, phenylmethyl or phenylethyl, $R_5$ is H;

X is CH, Y is $CONR_2$, $R_1$ is H, $CH_3$, $C_2H_5$ or $C_3H_7$, $R_2$ is H, $R_3$ is $(CH_2)_2$-phenyl, $R_4$ is morpholino, $R_5$ is H;

X is CH, Y is $NR_2CO$, $R_1$ is H, $CH_3$, $C_2H_5$ or $C_3H_7$, $R_2$ is H, $R_3$ is $(CH_2)_2$-phenyl;

X is CH, Y is $NR_2CO$, $R_1$ is H, $CH_3$, $C_2H_5$ or $C_3H_7$, $R_2$ is H, $R_3$ is $(CH_2)_2$-phenyl, $R_4$ is phenyl, phenylmethyl or phenylethyl, $R_5$ is H;

X is CH, Y is $NR_2CO$, $R_1$ is H, $CH_3$, $C_2H_5$ or $C_3H_7$, $R_2$ is H, $R_3$ is $CH_2$-phenyl, $R_4$ is morpholino, $R_5$ is H;

X is N, Y is $NR_2CO$, $R_1$ is H, $CH_3$, $C_2H_5$ or $C_3H_7$, $R_2$ is H, $R_3$ is phenyl, $R_4$ is $COR_8$, $R_8$ is morpholino;

X is CH, Y is $CONR_2$, $R_1$ is H, $CH_3$, $C_2H_5$ or $C_3H_7$, $R_2$ is H, $R_3$ is $(CH_2)_2$-phenyl;

X is CH, Y is $CONR_2$, $R_1$ is H, $CH_3$, $C_2H_5$ or $C_3H_7$, $R_2$ is H, $R_3$ is $(CH_2)_2$-phenyl, $R_4$ is phenyl, phenylmethyl or phenylethyl, $R_5$ is H;

X is CH, Y is $CONR_2$, $R_1$ is H, $CH_3$, $C_2H_5$ or $C_3H_7$, $R_2$ is H, $R_3$ is $CH_2$-phenyl, $R_4$ is morpholino, $R_5$ is H;

X is N, Y is $CONR_2$, $R_1$ is H, $CH_3$, $C_2H_5$ or $C_3H_7$, $R_2$ is H, $R_3$ is phenyl, $R_4$ is piperazinyl, $R_5$ is H;

X is CH, Y is $NR_2CO$, $R_1$ is H, $CH_3$, $C_2H_5$ or $C_3H_7$, $R_2$ is H, $R_3$ is phenyl;

X is N, Y is $NR_2CO$, $R_1$ is H, $CH_3$, $C_2H_5$ or $C_3H_7$, $R_2$ is H, $R_3$ is phenyl;

X is N, Y is $NR_2CO$, $R_1$ is H, $CH_3$, $C_2H_5$ or $C_3H_7$, $R_2$ is H, $R_3$ is $CH_2$-phenyl, $R_4$ is piperidino, $R_5$ is H;

X is N, Y is $CONR_2$, $R_1$ is H, $CH_3$, $C_2H_5$ or $C_3H_7$, $R_2$ is H, $R_3$ is $CH_2$-phenyl, $R_4$ is phenyl, phenylmethyl or phenylethyl, $R_5$ is H;

X is CH, Y is $CONR_2$, $R_1$ is H, $CH_3$, $C_2H_5$ or $C_3H_7$, $R_2$ is H, $R_3$ is $(CH_2)_2$-phenyl, $R_4$ is piperidino, $R_5$ is H;

X is N, Y is $NR_2CO$, $R_1$ is H, $CH_3$, $C_2H_5$ or $C_3H_7$, $R_2$ is H, $R_3$ is $CH_2$-phenyl, $R_4$ is morpholino, $R_5$ is H;

X is N, Y is $NR_2CO$, $R_1$ is H, $CH_3$, $C_2H_5$ or $C_3H_7$, $R_2$ is H, $R_3$ is phenyl, $R_4$ is piperazinyl, $R_5$ is H;

X is N, Y is $CONR_2$, $R_1$ is H, $CH_3$, $C_2H_5$ or $C_3H_7$, $R_2$ is H, $R_3$ is phenyl, $R_4$ is $COR_8$, $R_8$ is cyclohexyl;

X is N, Y is $CONR_2$, $R_1$ is H, $CH_3$, $C_2H_5$ or $C_3H_7$, $R_2$ is H, $R_3$ is phenyl;

X is N, Y is $NR_2CO$, $R_1$ is H, $CH_3$, $C_2H_5$ or $C_3H_7$, $R_2$ is H, $R_3$ is $CH_2$-phenyl.

Preferred compounds are:

(S)-N-[5-(4-Methylpiperazin-1-yl)-3,4-dihydro-2H-1-benzopyran-3-yl]-4-morpholinobenzamide (S)-N-[5-(4-Methylpiperazin-1-yl)-3,4-dihydro-2H-1-benzopyran-3-yl]-4-piperidinobenzamide (S)-N-[5-(4-Methylpiperazin-1-yl)-3,4-dihydro-2H-1-benzopyran-3-yl]-4-butoxybenzamide (S)-N-[5-(4-Methylpiperazin-1-yl)-3,4-dihydro-2H-1-benzopyran-3-yl]4-trifluoromethylbenzamide (S)-N-[5-(4-Methylpiperazin-1-yl)-3,4-dihydro-2H-1-benzopyran-3-yl]-4-N,N-diethylaminobenzamide (S)-N-[5-(4-Methylpiperazin-1-yl)-3,4-dihydro-2H-1-benzopyran-3-yl]-4-trifluoromethoxybenzamide (S)-N-[5-(4-Methylpiperazin-1-yl)-3,4-dihydro-2H-1-benzopyran-3-yl]4-(4-piperidon-1-yl)benzamide (S)-N-[5-(4-Methylpiperazin-1-yl)-3,4-dihydro-2H-1-benzopyran-3-yl]-4-(hexahydro-1,4-diazepin-5-on-1-yl)benzamide, and (S)-N-[5-(4-Methylpiperazin-1-yl)-3,4-dihydro-2H-1-benzopyran-3-yl]-4-(4-benzylpiperazin-1-yl)benzamide.

The compounds of the present invention are in the form of the racemate or the (R)- or (S)-enantiomer in the form of a free base or a pharmaceutically acceptable salt or solvate thereof. Compounds in the form of the (S)-enantiomer are preferred ones.

Both organic and inorganic acids can be employed to form non-toxic pharmaceutically acceptable acid addition salts of the compounds of this invention. Illustrative acids are sulfuric, nitric, phosphoric, oxalic, hydrochloric, formic, hydrobromic, citric, acetic, lactic, tartaric, dibenzoyltartaric, diacetyltartaric, palmoic, ethanedisulfonic, sulfamic, succinic, propionic, glycolic, malic, gluconic, pyruvic, phenylacetic, 4-aminobenzoic, anthranilic, salicylic, 4-aminosalicylic, 4-hydroxybenzoic, 3,4-dihydroxybenzoic, 3,5-dihydroxybenzoic, 3-hydroxy-2-naphthoic, nicotinic, methanesulfonic, ethanesulfonic, hydroxyethanesulfonic, benzenesulfonic, p-toluenesulfonic, sulfanilic, naphthalenesulfonic, ascorbic, cyclohexylsulfamic, fumaric, maleic and benzoic acids. These salts are readily prepared by methods known in the art.

The preferred solvates of the compounds of this invention are the hydrates.

PHARMACEUTICAL FORMULATIONS

In a second aspect the present invention provides a pharmaceutical formulation comprising as active ingredient a therapeutically effective amount of the compound of formula I as an enantiomer or a racemate in the form of a free base or a pharmaceutically acceptable salt or solvate thereof, optionally in association with diluents, excipients or inert carriers.

According to the present invention the compound of the invention will normally be administered orally, rectally or by injection, in the form of pharmaceutical formulations comprising the active ingredient either as a free base or a pharmaceutically acceptable non-toxic acid addition salt, e.g. the hydrochloride, hydrobromide, lactate, acetate, phosphate, sulfate, sulfamate, citrate, tartrate, oxalate and the like in a pharmaceutically acceptable dosage form. The dosage form may be a solid, semisolid or liquid preparation.

Usually the active substance will constitute between 0.1 and 99% by weight of the preparation, more specifically between 0.5 and 20% by weight for preparations intended for injection and between 0.2 and 50% by weight for preparations suitable for oral administration.

To produce pharmaceutical formulations containing the compound of the invention in the form of dosage units for oral application, the selected compound may be mixed with a solid excipient, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain, e.g. gum arabic, gelatine, talcum, titanium dioxide, and the like. Alternatively, the tablet can be coated with a polymer known to the person skilled in the art, dissolved in a readily volatile organic solvent or mixture of organic solvents. Dyestuffs may be added to these coatings in order to readily distinguish between tablets containing different active substances or different amounts of the active compound.

For the preparation of soft gelatine capsules, the active substance may be admixed with e.g. a vegetable oil or poly-ethylene glycol. Hard gelatine capsules may contain granules of the active substance using either the above mentioned excipients for tablets, e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Dosage units for rectal application can be solutions or suspensions or can be prepared in the form of suppositories comprising the active substance in a mixture with a neutral fatty base, or gelatine rectal capsules comprising the active substance in admixture with vegetable oil or paraffin oil. Liquid preparations for oral application may be in the form of syrups or suspensions, for example solutions containing from about 0.1% to about 20% by weight of the active substance herein described, the balance being sugar and mixture of ethanol, water, glycerol and propylene glycol. Optionally such liquid preparations may cod tain colouring agents, flavouring agents, saccharin carboxymethyl-cellulose as a thickening agent or other excipients known to the person skilled in the art.

Solutions for parenteral applications by injection can be prepared in an aqueous solution of a water-soluble pharmaceutically acceptable salt of the active substance, preferably in a concentration of from about 0.1% to about 10% by weight. These solutions may also contain stabilizing agents and/or buffering agents and may conveniently be provided in various dosage unit ampoules.

Suitable daily doses of the compound of the invention in therapeutical treatment of humans are about 0.01–100 mg/kg bodyweight at peroral administration and 0.001–100 mg/kg bodyweight at parenteral administration.

The compound of the invention may be used in a combination with a 5-HT reuptake inhibitor, such as fluoxetine, paroxetine, citalopram, clomipramine, sertraline, alaproclate or fluvoxamin, preferably paroxetine or citalopram. Another possible combination is to use the compound of the invention together with a monoamine oxidase inhibitor, such as moclobemide, tranylcypramine, brofaromide or phenelzine, preferably moclobemide or phenelzine. Still another possible combination is the compound of the invention together with a 5-HT$_{1A}$ antagonist, such as the compounds disclosed in WO 96/33710, preferably (R)-5-carbamoyl-3-(N,N-dicyclobutylamino)-8-fluoro-3,4-dihydro-2H-1-benzopyran.

MEDICAL AND PHARMACEUTICAL USE

In a further aspect the present invention provides the use of the compounds of formula I in therapy as a h5-HT$_{1B}$ antagonist, partial agonist or full agonist, preferably as an antagonist and the use in the treatment of 5-hydroxytryptamine mediated disorders. Examples of such disorders are disorders in the CNS such as mood disorders (depression, major depressive episodes, dysthymia, seasonal affective disorder, depressive phases of bipolar disorder), anxiety disorders (obsessive compulsive disorder, panic disorder with/without agoraphobia, social phobia, specific phobia, generalized anxiety disorder, posttraumatic stress disorder), personality disorders (disorders of impulse control, trichotellomania), obesity, anorexia, bulimia, premenstrual syndrome, sexual disturbances, alcoholism, tobacco abuse, autism, attention deficit, hyperactivity disorder, migraine, memory disorders (age associated memory impairment, presenile and senile dementia), pathological aggression, schizophrenia, endocrine disorders (e.g. hyperprolactinaemia), stroke, dyskinesia, Parkinson's disease, thermoregulation, pain and hypertension. Other examples of hydroxytryptamine mediated disorders are urinary incontinence, vasospasm and growth control of tumors (e.g. lung carcinoma).

METHODS OF PREPARATION

The present invention also relates to processes for preparing the compound of formula I. Throughout the following description of such processes it is understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis" T. W. Greene, Wiley-Interscience, New York, 1991.

METHODS OF PREPARATION OF INTERMEDIATES

1. In the Case where Y is NR$_2$CO and X is N (i) Benzylation of the compound of the formula II, described in: Thorberg S-O.; Hall H.; Åkesson C.; Svensson K.; Nilsson J. L. G. *Acta Pharm. Suec.* 1987, 24(4), 169–182 as a racemate or in the patent application WO 93/07135 as an enantiomer,

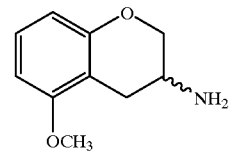

(II)

to obtain a compound of formula III may be carried out by reaction with a suitable benzylation agent e.g. a benzyl halide such as benzyl bromide or benzyl chloride or an activated alcohol, e.g. benzyl mesylate or benzyl tosylate. The reaction may be carried out using a salt or the base of compound II in a suitable solvent, e.g. N,N-dimethylformamide, acetone or acetonitrile, with a suitable base, e.g. NaOH, NaHCO₃, K₂CO₃ or a triakylamine such as triethylamine, at a temperature within the range of +20° C. to +150° C. The presence of a suitable catalyst, e.g. potassium iodide or sodium iodide, may increase the speed of the reaction.

(ii) Demethylation of the compound of formula III

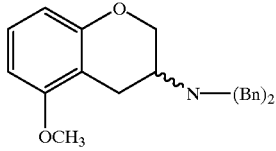

(III)

to obtain a compound of formula IV may be carried out by treating the compound with an acidic reagent such as aqueous HBr, HI, HBr/CH₃COOH, BBr₃, AlCl₃, pyridine-HCl or with a basic nucleophilic reagent such as CH₃C₆H₄S⁻ or C₂H₅S⁻ in a suitable solvent. Suitable solvents may be methylene chloride or chloroform and the reaction may occur between −78° C. and +60° C.

(iii) Conversion of the compound of formula IV to a compound of formula V

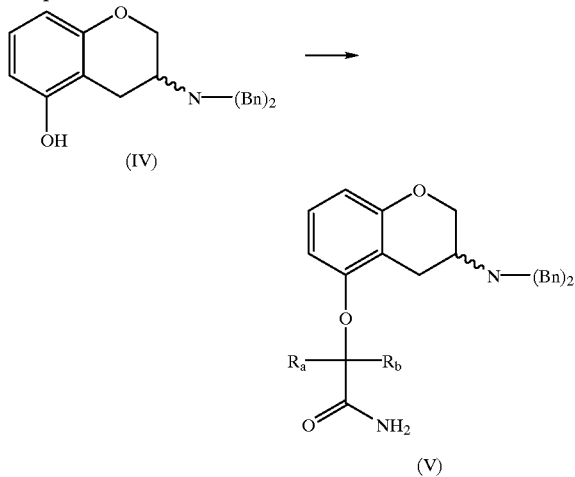

may be carried out by the reaction with a compound of formula VI (VI)

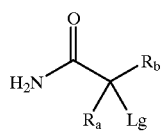

where Lg denotes for a leaving group, e.g. a halogen such as chlorine, bromine or iodine or an alkane- or arenesulfonyloxy group such as a p-toluenesulfonyloxy group and $R_a$ and $R_b$ are hydrogen or a lower alkyl group, e.g. methyl. The process may be carried out with a salt of the compound of formula IV obtained by reaction with a base such as K₂CO₃, Na₂CO₃, KOH, NaOH, BuLi or NaH. The reaction may be conducted in a suitable solvent e.g. an aprotic solvent such as dioxane, N,N-dimethylformamide, tetrahydrofuran, toluene, benzene or petroleum ether and the reaction may occur between +20° C. and +150° C.

(iv) Rearrangement of a compound of formula V to a compound of formula VII

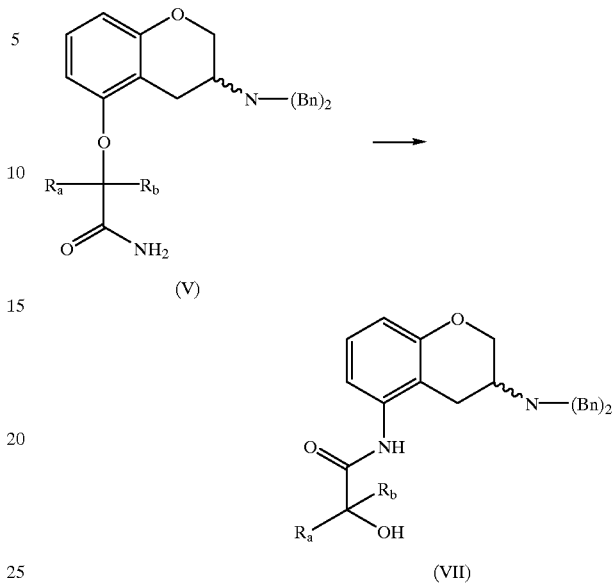

may be carried out in a suitable solvent, e.g. aprotic solvent such as N,N-dimethylformamide, dioxane, 1,1,3,3-tetramethylurea, tetrahydrofuran or hexamethylphosphoric triamide, with a suitable base, e.g. K₂CO₃, KOH, potassium tert-butoxide or NaH, at a temperature within the range of +20° C. to +150° C. The presence of a cosolvent such as 1,3-dimethyl-3,4,5,6-tetrahydro-2(1H)-pyrimidone or hexamethyl-phosphoric triamide in appropriate concentration in the solvent may increase the speed of the reaction.

(v) Hydrolysis of a compound of formula VII to a compound VIII may be carried out under acidic conditions using acids such as H₂SO₄, HCl or HBr in a suitable solvent, e.g. H₂O, ethanol, methanol or mixtures thereof, and the reaction may occur between +20° C. and +100° C. or under basic conditions using bases such as NaOH or KOH in a suitable solvent, e.g. H₂O, ethanol, methanol or mixtures thereof, and the reaction may occur between +20° C. and +100° C.

(vi) Conversion of compound of formula VIII to a compound of formula IX

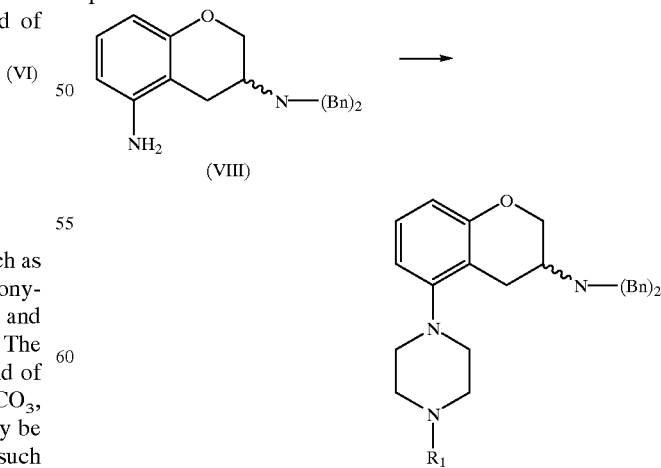

may be carried out by
a) reaction with a compound of formula X

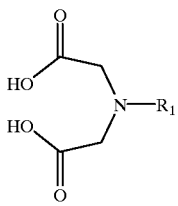

(X)

where $R_1$ is $C_1$–$C_6$ alkyl or $C_3$–$C_6$ cycloalkyl. The process may be carried out in a suitable solvent, e.g. an aprotic/anhydrous solvent such as tetrahydrofuran or N,N-dimethylformamide, in the presence of coupling reagent such as N,N'-carbonyldiimidazole and the reaction may occur between +20° C. and +130° C. The reaction is followed by the reduction of the imide with a suitable reducing agent, e.g. LiAlH$_4$, in a suitable solvent, e.g. diethyl ether or tetrahydrofuran at a temperature between +20° C. and reflux, or b) by reaction with a compound of formula XI

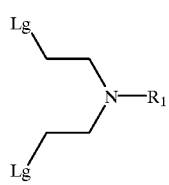

(XI)

where Lg denotes a leaving group, e.g. a halogen such as chlorine, bromine or iodine or an alkane- or arenesulfonyloxy group such as p-toluenesulfonyloxy group and $R_1$ is hydrogen, $C_1$–$C_6$-alkyl or $C_3$–$C_6$ cycloalkyl. The process may be carried out in a suitable solvent such as ethanol, buthanol, N,N-dimethylformamide, acetonitrile or a mixture of water and acetonitrile with a suitable base, e.g. $K_2CO_3$, $NaHCO_3$ or KOH, and the reaction may occur between +20° C. and +150° C.

(vii) Conversion of the compound of formula IX to a compound of formula XII

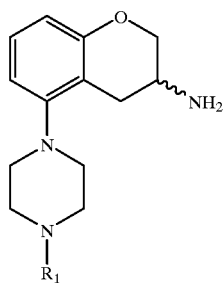

(XII)

where $R_1$ is $C_1$–$C_6$ alkyl or $C_3$–$C_6$ cycloalkyl may be carried out by
a) hydrogenation using a catalyst containing palladium, platinum, rhodium or nickel in a suitable solvent, e.g. acetic acid or ethanol and at a reaction temperature between +20° C. and +120° C., or
b) debenzylation in a suitable solvent such as methanol in the presence of ammonium formate and Pd/C and at a reaction temperature between +20° C. and reflux.

(viii) Conversion of a compound of formula IX, where $R_1$ is hydrogen, to a compound of formula XIII,

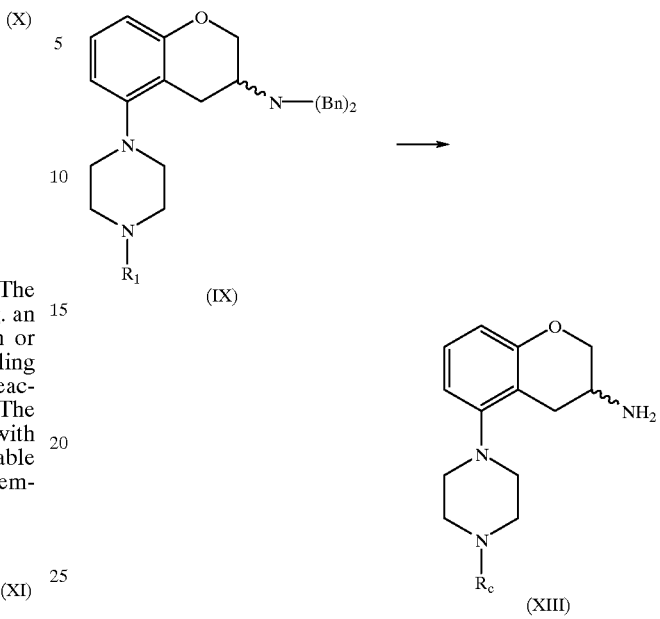

where $R_c$ denotes a suitable protecting group, may be carried out by
a) hydrogenation using a catalyst containing palladium, platinum, rhodium or nickel in a suitable solvent, e.g. acetic acid or ethanol, at a reaction temperature between +20° C. and +120° C., or
b) debenzylation in a suitable solvent such as methanol in the presence of ammonium formate and Pd/C at a reaction temperature between +20° C. and reflux.

Said reaction is followed by the protection of the piperazine ring in a suitable solvent, e.g. methylene chloride or chloroform, with an appropriate protecting reagent e.g. di-tert-butyl dicarbonate with a suitable base, e.g. triethylamine or $K_2CO_3$, and at a temperature between −20° C. and +60° C., resulting in compound of formula XIII.

2. In the Case where Y is $NR_2CO$ and X is CH
(i) Halogenation of the compound of formula XIV, either as a racemate (described in: Thorberg S-O.; Hall H.; Åkesson C.; Svensson K.; Nilsson J. L. G. *Acta Pharm. Suec.* 1987, 24(4), 169–182), or as an enantiomer

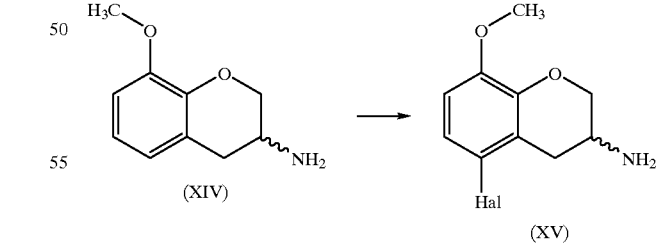

to obtain a compound of formula XV may be performed by aromatic electrophilic substitution using a suitable halogenation agent such as $Br_2$, $Cl_2$, $I_2$, ICl, or $SO_2Cl_2$. The reaction may be carried out using the salt or the base of the compound XIV in an appropriate solvent, e.g. acetic acid, HCl/ethanol or water, with or without a suitable base, e.g. an alkali metal acetate such as sodium acetate and at a reaction temperature between −20° C. and room temperature.

(XVI)

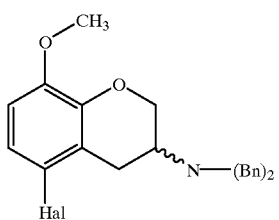

(ii) Benzylation of the compound of the formula XV, either as a racemate or as an enantiomer, to obtain a compound of the formula XVI may be carried out by reaction with a suitable benzylation agent, e.g. benzyl halide such as benzyl bromide or benzyl chloride. The reaction may be carried out using the salt or the base of compound XV in a suitable solvent, e.g. N,N-dimethylformamide, acetone or acetonitrile, with a suitable base such as triethylamine, NaOH, NaHCO$_3$ or K$_2$CO$_3$ at a temperature within the range of +20° C. to +150° C. The presence of a suitable catalyst, e.g. an alkali metal halide such as potassium iodide or sodium iodide, may increase the speed of the reaction.

(XVII)

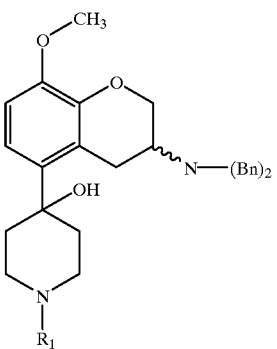

(iii) The conversion of the compound of the formula XVI to the compound of the formula XVII, where R$_1$ is C$_1$–C$_6$ alkyl or C$_3$–C$_6$ cycloalkyl, may be performed by a metal-halogen exchange, in an appropriate anhydrous solvent such as tetrahydrofuran or diethyl ether using a suitable alkyl-lithium or metal, e.g. butyllithium, lithium or magnesium turnings, followed by treatment with an appropriate piperidone such as N-methyl-4-piperidone and a subsequent suitable workup. The reaction may be performed at a reaction temperature within the range of −78° C. to room temperature.

(XVIII)

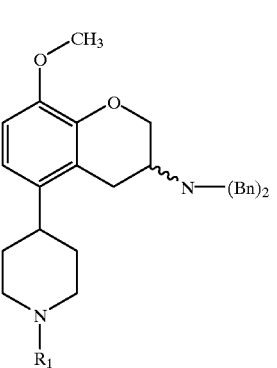

(iv) The compound of the formula XVII may be reduced to the compound of the formula XVIII by treatment with a suitable reducing agent such as sodium borohydride and a protonating agent such as CF$_3$COOH, CF$_3$SO$_3$H or HCOOH in an appropriate solvent such as tetrahydrofuran or diethyl ether. The reaction may be performed at reaction temperature between 0° C. and reflux.

(XIX)

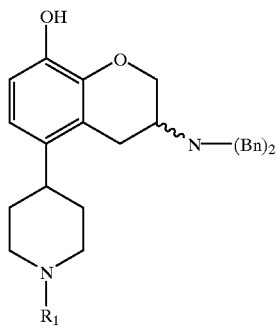

(v) Demethylation of the compound of the formula XVIII to obtain a compound of formula XIX may be performed by treating the compound with an acidic reagent such as aqueous HBr, HI, HBr/acetic acid, BBr$_3$, AlCl$_3$, pyridine-HCl or with a basic nucleophilic reagent such as C$_2$H$_5$S$^-$ or CH$_3$C$_6$H$_4$S$^-$ in a suitable solvent. Suitable solvents may be methylene chloride or chloroform and the reaction may occur between −78° C. and +60° C.

(XX)

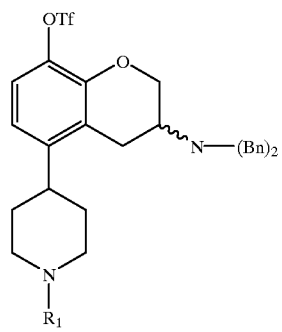

(vi) Conversion of the compound of formula XIX to a compound of formula XX may be carried out with a compound such as trifluoromethanesulfonic anhydride in a suitable solvent such as methylene chloride or carbon tetrachloride in the presence of a base such as 2,4,6-collidine, triethylamine or pyridine at a reaction temperature within the range of −78° C. to room temperature.

(XXI)

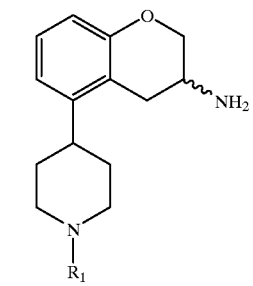

(vii) Conversion of the compound of formula XX to a compound of formula XXI may be performed by
  a) hydrogenation using a catalyst such as palladium, platinum, rhodium or nickel in a suitable solvent such as acetic acid or ethanol at a reaction temperature between +20° C. and +120° C., or
  b) reaction in a suitable solvent such as methanol in the presence of ammonium formate and Pd/C at a reaction temperature between +20° C. and reflux.

3. In the Case where Y is $CONR_2$ and X is N (i) Nitration of a compound of formula XXII either as a racemate (described in: Thorberg S-O.; Hall H.; Åkesson C.; Svensson K.; Nilsson J. L. G. *Acta Pharm. Suec.* 1987, 24(4), 169–182), or as an enantiomer to obtain a compound of formula XXIII,

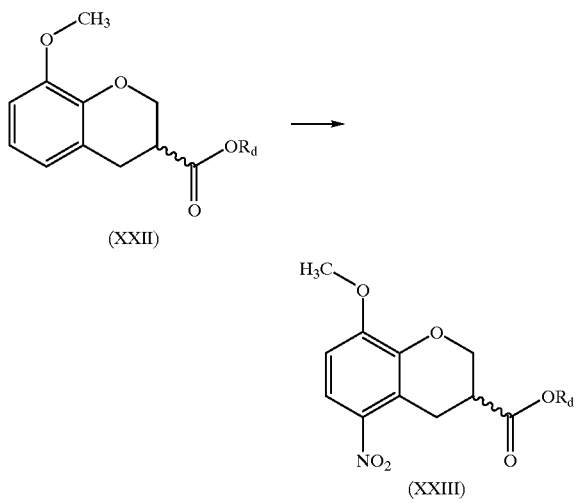

where $R_d$ is $C_1$–$C_6$ alkyl, may be carried out by aromatic electrophilic substitution using a suitable nitration reagent such as nitric acid or nitric acid and sulfuric acid in a suitable solvent, e.g. acetic acid, acetic anhydride or water, at a reaction temperature between −20° C. and room temperature.

(ii) Demethylation of the compound of the formula XXIII to obtain a compound of formula XXIV

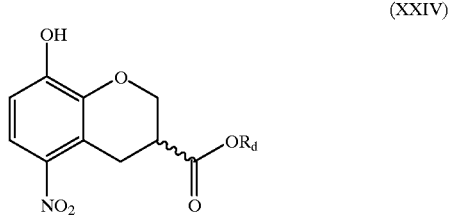

may be carried out by treating the compound with an acidic reagent such as aqueous HBr, HI, HBr/$CH_3COOH$, $BBr_3$, $AlCl_3$, pyridine-HCl or with a basic nucleophilic reagent such as $CH_3C_6H_4S^−$ or $C_2H_5S^−$. Suitable solvents may be methylene chloride or chloroform and the reaction may occur between −78° C. and +60° C.

During the demethylation of XXIII, hydrolysis of the ester may occur and the acid function could then be converted back to the ester by methods known by a person skilled in the art (See T. W. Greene, Wiley-Interscience, New York, 1991).

(iii) Conversion of the compound of formula XXIV to a compound of formula XXV

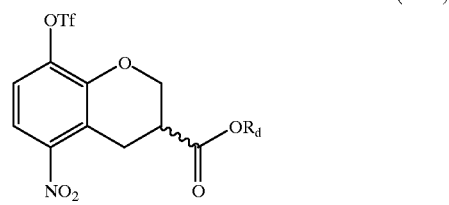

may be carried out by the reaction with an activated trifluoromethanesulfonic reagent e.g. trifluoromethanesulfonic anhydride in a suitable solvent such as methylene chloride, chloroform or carbon tetrachloride in the presence of a suitable base such as triethylamine, pyridine or 2,4,6-collidine at a reaction temperature between −78° C. and room temperature.

(iv) Conversion of the compound of formula XXV to a compound of formula XXVI may be carried out by

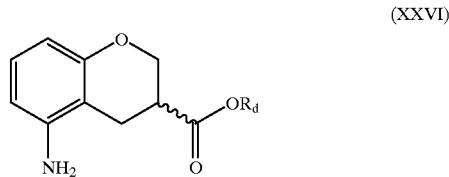

a) hydrogenation using a catalyst containing palladium, platinum or nickel in a suitable solvent such as ethanol, methanol or acetic acid and at a reaction temperature between +20° C. and +120° C. or
  b) reaction in a suitable solvent such as methanol in the presence of a ammonium formate such as triethyl ammonium formate and Pd/C and at a reaction temperature between +20° C. and reflux.

(v) Conversion of the compound of formula XXVI to a compound of formula XXVII

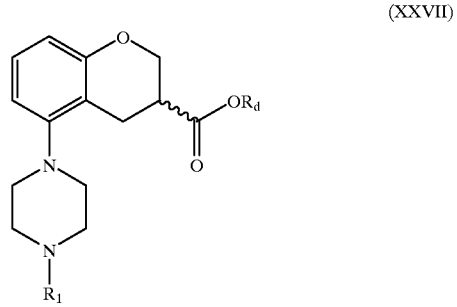

may be carried out by reaction of compound XI

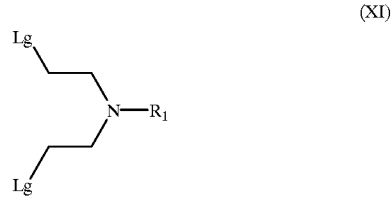

where Lg denotes a leaving group, e.g. a halogen such as chlorine, bromine or iodine, or an alkane- or arenesulfonyloxy group such as p-toluenesulfonyloxy group and $R_1$ is hydrogen, $C_1$–$C_6$ alkyl or $C_3$–$C_6$ cycloalkyl. The process may be carried out in a suitable solvent such as ethanol, buthanol, N,N-dimethylformamide, acetonitrile or a mixture of water and acetonitrile with a suitable base, e.g. $K_2CO_3$, $NaHCO_3$ or KOH, and the reaction may occur between +20° C. and +150° C. During the cyclization reaction of XXVI, hydrolysis the ester may occur.

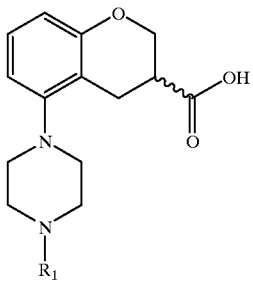

(XXVIII)

(vi) Hydrolysis of a compound of formula XXVII may be carried out under acidic is conditions using acids such as $H_2SO_4$, HCl, HBr, in a suitable solvent such as $H_2O$, ethanol, methanol, acetic acid or mixtures thereof at a temperature between +20° C. and reflux or under basic conditions using bases such as NaOH or KOH in a suitable solvent such as as $H_2O$, ethanol, methanol or mixtures thereof at a temperature between +20° C. and reflux, resulting in a compound of formula XXVIII, where $R_1$ is hydrogen, $C_1$–$C_6$ alkyl or $C_3$–$C_6$ cycloalkyl.

(vii) When $R_1$ is hydrogen, protection of a compound of formula XXVIII as a compound of formula XXIX where $R_c$ is a protecting group

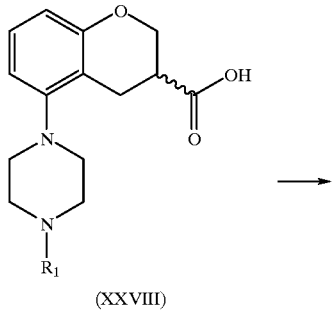

(XXVIII)

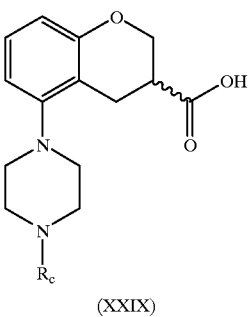

(XXIX)

may be carried out by the reaction with a suitable protecting reagent such as di-tert-butyl dicarbonate in a suitable solvent, e.g methylene chloride or chloroform, with a suitable base such as triethylamine or $K_2CO_3$ and at a temperature between −20° C. and +60° C. 4.

(i) Conversion of a compound of formula XXX to a compound of formula XXXI

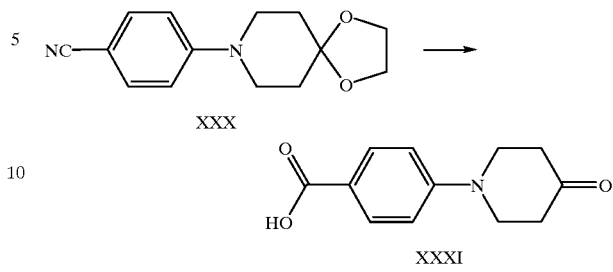

may be carried out by a) hydrolysis of the nitrile in compound of formula XXX in a suitable solvent such as aqueous methanol or aqueous ethanol in the presence of a suitable base such as NaOH or KOH at a reaction temperature between room temperature and reflux, followed by b) hydrolysis of the above formed amide and the ketal under acidic conditions in a suitable solvent such as aqueous methanol, aqueous ethanol or water in the presence of a suitable acid such as HCl or HBr at a reaction temperature between room temperature and reflux.

(ii) Conversion of a compound of formula XXXI to a compound of formula XXXII

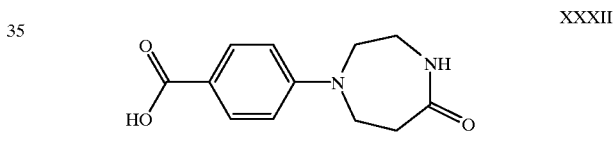

may be carried out by reaction with a suitable azide such as sodium azide in a suitable acid or mixtures of acids such as $H_2SO_4$ and acetic acid at a reaction temperature between 0° C. and +50° C.

(iii) Conversion of a compound of formula XXXIII to a compound of formula XXXIV

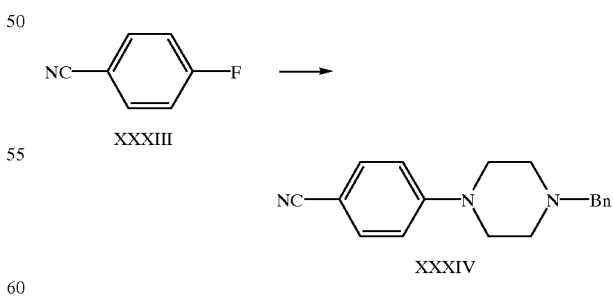

may be carried out by reaction with 1-benzylpiperazine in a suitable solvent such as N,N-dimethylformamide, dimethylsulfoxide or acetonitrile in the presence of a suitable base such as KOH or $K_2CO_3$ at a reaction temperature between +50° C. and +150° C.

(XXXV)

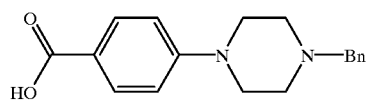

(iv) Hydrolysis of a compound of formula XXXIV to a compound XXXV may be carried out under acidic conditions using acids such as $H_2SO_4$, HCl or HBr in a suitable solvent, e.g. $H_2O$, ethanol, methanol or mixtures thereof, and the reaction may occur between +20° C. and +100° C. or under basic conditions using bases such as NaOH or KOH in a suitable solvent, e.g. $H_2O$, ethanol, methanol or mixtures thereof, and the reaction may occur between +20° C. and +100° C.

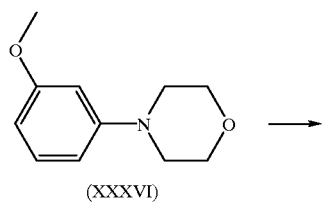

(XXXVI)

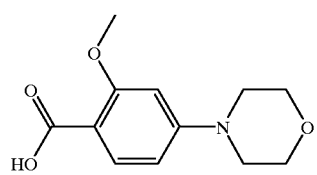

(XXXVII)

(v) Halogenation of a compound of formula XXXVI to a compound of formula XXXVII where Hal denotes bromine, chlorine or iodine may be performed by a reagent such as ICl or $Br_2$, $Cl_2$ or $SO_2Cl_2$ with a suitable base such as sodium acetate in a suitable solvent such as acetic acid at a reaction temperature between +20° C. and +50° C.

(v) Conversion of a compound of formula XXXVII to a compound of formula XXXVIII

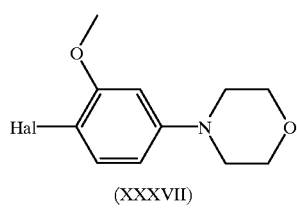

(XXXVIII)

may be carried out by a metal-halogen exchange, in an appropriate anhydrous solvent such as tetrahydrofuran or diethyl ether using a suitable alkyl-lithium or metal, e.g. butyllithium, lithium or magnesium turnings, followed by treatment with carbon dioxide at a reaction temperature between −78° C. and room temperature.

METHODS OF PREPARATION OF END PRODUCTS

Another object of the invention is a process A(i), A(ii), A(iii), B(i), B(ii) or C for the preparation of the compound of general formula I by A(i)

acylation, in the case when $R_1$ is $C_1$–$C_6$ alkyl or $C_3C_6$ cycloalkyl, Y is $NR_2CO$, $R_2$ is hydrogen and X and $R_3$ are as defined in general formula I above, of a compound of formula A,

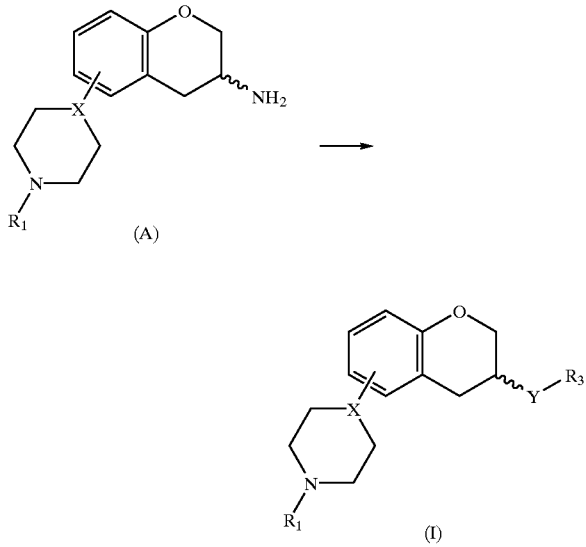

with an activated carboxylic acid $R_3$—$COLg_1$ where $Lg_1$ is a leaving group or by using a carboxylic acid $R_3$—COOH with an activating reagent.

Thus, the acylation according to the process A(i) may be carried out with an appropriate activated carboxylic acid, $R_3COLg_1$ where $R_3$ is as defined above and $Lg_1$ is a leaving group, such as halogen, e.g. chlorine, in a suitable solvent such as methylene chloride or chloroform with a suitable base, e.g. a trialkylamine such as triethylamine, at a temperature between −20° C. and reflux temperature or by using an carboxylic acid, $R_3COOH$ wherein $R_3$ is as defined above with an activating reagent, e.g. N,N'-carbonyldiimidazole, N,N'-dicyclohexylcarbodiimide or diphenylphosphinic chloride, with a suitable base such as N-methylmorpholine in a suitable solvent such as N,N-dimethylformamide or tetrahydrofuran and the reaction may be conducted at a temperature between +20° C. and +150° C.

A(ii)

acylation, in the case when $R_1$ is hydrogen, Y is $NR_2CO$, $R_2$ is hydrogen, $R_c$, is a protecting group and X and $R_3$ are as defined in general formula I above, of a compound of formula B

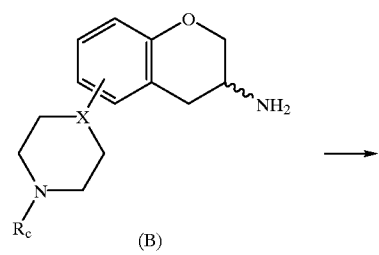

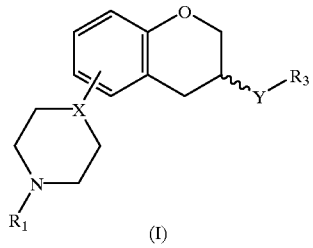

(I)

with an activated carboxylic acid $R_3$—$COLg_1$ where $Lg_1$ is a leaving group or by using a carboxylic acid $R_3$—COOH with an activating reagent, followed by the removal of the protecting group $R_c$;

Thus, the acylation according to the process A(ii) may be carried out with an appropriate activated carboxylic acid, $R_3COLg_1$ where $R_3$ is as defined above and $Lg_1$ is a leaving group, such as halogen, e.g. chlorine, in a suitable solvent such as methylene chloride or chloroform with a suitable base, e.g. a trialkylamine such as triethylamine, or by using a carboxylic acid, $R_3COOH$ where $R_3$ is defined as above, with an activating reagent, e.g. N,N'-carbonyldiimidazole, N,N'-dicyclohexylcarbodiimide or diphenylphosphinic chloride, with a suitable base such as N-methylmorpholine in a suitable solvent such as N,N-dimethylformamide or tetrahydrofuran and the reaction may be conducted at a temperature between +20° C. and +150° C., followed by removal of the protecting group $R_c$ by hydrolysis in a suitable solvent such as methylene chloride or chloroform with a suitable acid such as trifluoroacetic acid at a temperature between +20° C. and +60° C.

A(iii)

debenzylation, in the case when $R_1$ is $C_1$–$C_6$ alkyl or $C_3$–$C_6$ cycloalkyl, X and $R_2$ is as defined in general formula I above and $R_9$ below is $C_1$–$C_6$ alkyl, $C_3$–$C_6$ cycloalkyl, $(CH_2)_mOH$ wherein m is 2–6 or $COR_8$, of a compound of formula Ia, followed by a) hydrogenation, b) alkylation, c) alkylation and removal of a protecting group or
d) acylation;

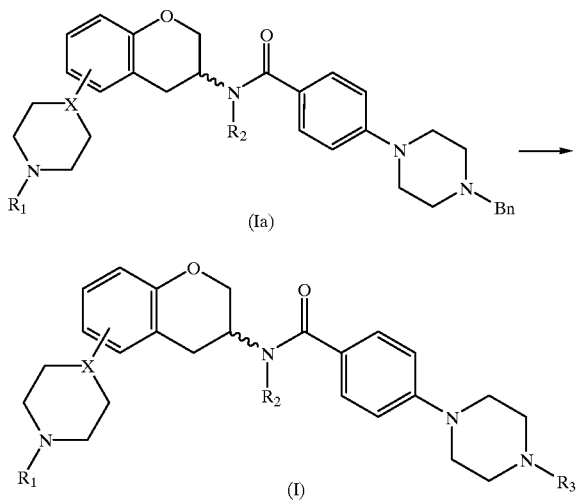

Thus, in the case when $R_9$ is H the hydrogenation a) above of a compound of formula Ia may be carried out by using a catalyst such as palladium, platinum, rhodium or nickel in a suitable solvent such as acetic acid or ethanol at a reaction temperature between +20° C. and +120° C., or reaction in a suitable solvent such as methanol in the presence of ammonium formate and Pd/C at a reaction temperature between +20° C. and reflux.

In the case when $R_9$ is $C_1$–$C_6$ alkyl or $C_3$–$C_6$ cycloalkyl the debenzylation is followed by the alkylation b) above using a suitable alkylation reagent such as $R_1$—Lg where Lg is a suitable leaving group, e.g. a halogen such as chlorine, bromine or iodine, or an alkane- or arenesulfonyloxy group such as a p-toluenesulfonyloxy group and $R_1$ is $C_1$–$C_6$ alkyl. The reaction may be carried out in a suitable solvent such as N,N-dimethylformamide, acetone, acetonitrile or tetrahydrofuran with a suitable base such as $K_2CO_3$, $NaHCO_3$, NaOH or a trialkylamine such as triethylamine. The reaction may be conducted at a temperature between +20° C. and +120° C. or, reductive alkylation with a compound $R_1$—CHO, where $R_1$ is hydrogen or $C_1$–$C_5$ alkyl, or with a $C_3$–$C_6$ cyclic ketone, in the presence of a reductive agent such as sodium cyanoborohydride, sodium borohydride or catalytically with $H_2$ and a suitable catalyst containing palladium, platinum, rhodium or nickel in a suitable solvent, e.g. tetrahydrofuran, dioxane, methanol or ethanol. A proton donor such as p-toluenesulfonic acid can be used to catalyze the formation of the imine/enamine and adjustment of pH to slightly acidic by an appropriate acid such as acetic acid may speed up the reaction.

In the case when $R_9$ is $(CH_2)_mOH$ and m is 2–6, the debenzylation is followed by the alkylation c) above by using a suitable alkylation reagent such as $BnO(CH_2)_mLg$ where Lg is a suitable leaving group, e.g. a halogen such as chlorine, bromine or iodine, or an alkane- or arenesulfonyloxy group such as a p-toluenesulfonyloxy group and $R_1$ is $C_1$–$C_6$ alkyl. The reaction may be carried out in a suitable solvent such as N,N-dimethylformamide, acetone, acetonitrile or tetrahydrofuran with a suitable base such as $K_2CO_3$, $NaHCO_3$, NaOH or a trialkylamine such as triethylamine and may be conducted at a temperature between +20° C. and +120° C. The reaction is followed by removal of a protecting group, such as a benzyl group, by hydrogenation using a catalyst such as palladium, platinum, rhodium or nickel in a suitable solvent such as acetic acid or ethanol at a reaction temperature between +20° C. and +120° C., or reaction in a suitable solvent such as methanol in the presence of ammonium formate and Pd/C at a reaction temperature between +20° C. and reflux.

In the case when $R_9$ is $COR_8$ the debenzylation is followed by the acylation d) above by using an appropriate activated carboxylic acid, $R_8COLg_1$ where $R_8$ is as defined above and $Lg_1$ is a leaving group, such as halogen, e.g. chlorine, in a suitable solvent such as methylene chloride, chloroform or N,N-dimethylformamide with a suitable base, e.g. a trialkylamine such as triethylamine or by using a carboxylic acid, $R_6COOH$ where $R_6$ is defined as above, with an activating reagent, e.g. N,N'-carbonyldiimidazole, N,N'-dicyclohexylcarbodiimide or diphenylphosphinic chloride, with a suitable base such as N-methylmorpholine in a suitable solvent such as N,N-dimethylformamide or tetrahydrofuran and the reaction may be conducted at a temperature between +20° C. and +150° C.

B(i)

reacting, in the case when $R_1$ is $C_1$–$C_6$ alkyl or $C_3$–$C_6$ cycloalkyl, Y is $CONR_2$, X, $R_2$ and $R_3$ are as defined in general formula I above, an activated carboxylic acid of a compound of formula C,

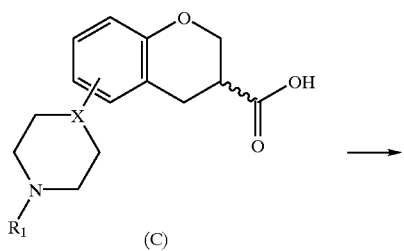

(C)

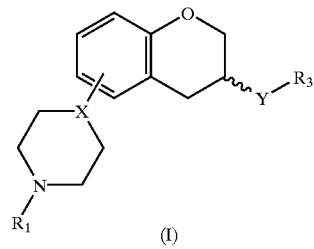

(I)

with an aniline or amine $HNR_2R_3$.

Thus, conversion according to the process B(i) of a compound of formula C may be carried out by activation of the acid function of a compound as an acid halide such as an acid chloride or by using an activating reagent such as N,N'-carbonyldiimidazole or N,N-dicyclohexylcarbodiimide in a suitable solvent, e.g. methylene chloride, chloroform, toluene, N,N-dimethylformamide, dioxane or tetrahydrofuran, followed by the addition of an appropriate amine or aniline $HNR_2R_3$ and the reaction may occur between 0° C. and +120° C.

B(ii)

reacting, in the case when $R_1$ is hydrogen, Y is $NR_2CO$, $R_c$ is a protecting group and X, $R_2$ and $R_3$ are as defined in general formula I above, an activated carboxylic acid of a compound of formula D

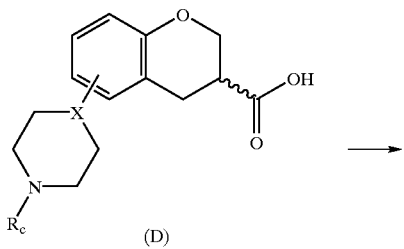

(D)

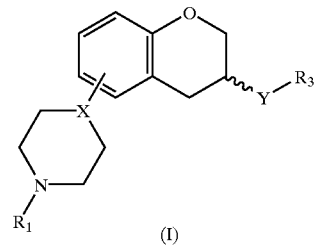

(I)

with an aniline or amine $HNR_2R_3$, followed by removal of the protecting group $R_c$.

Thus, conversion according to the process B(ii), of a compound of formula D, may be carried out by activation of the acid function of a compound as an acid halide such as an acid chloride or by using an activating reagent such as N,N'-carbonyldiimidazole or N,N-dicyclohexylcarbodiimide in a suitable solvent, e.g. methylene chloride, chloroform, toluene, N,N-dimethylformamide, dioxane or tetrahydrofuran, followed by the addition of an appropriate amine or aniline $HNR_2R_3$ and the reaction may occur between 0° C. and +120° C., followed by removal of the protecting group $R_c$ by methods known by a person skilled in the art such as hydrolysis in a suitable solvent such as methylene chloride or chloroform with a suitable acid, e.g. trifluoroacetic acid, at a temperature between +20° C. and +60° C.

C reaction, in the case when $R_1$ is $C_1$–$C_6$ alkyl or $C_3$–$C_6$ cycloalkyl, Y is $NR_2CONR_2$, $R_2$ is hydrogen and X and $R_3$ are as defined in general formula I above, a compound of formula A,

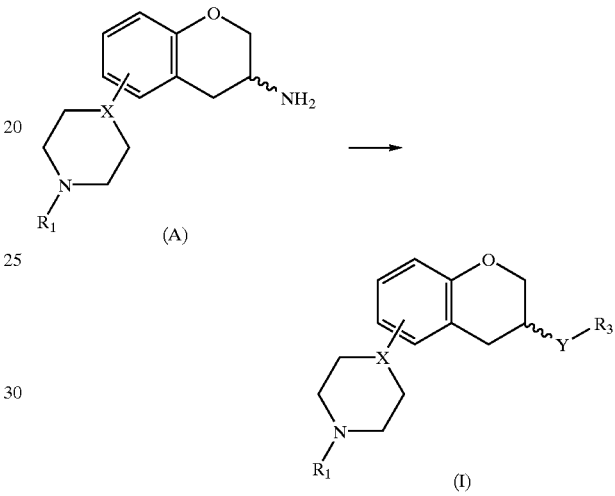

with a suitable azide in the presence of carboxylic acid, $R_3COOH$.

Thus, reaction according to the process C may be carried out with an appropriate azide such as diphenylphosphoryl azide in the presence of a carboxylic acid, $R_3COOH$ where $R_3$ is as defined above in a suitable solvent such as acetonitrile and the reaction may be conducted at a temperature between +20° C. and reflux temperature.

INTERMEDIATES

Another object of the invention is a compound having the formula

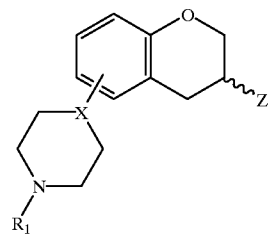

wherein

X=N or CH;

Z=$NH_2$ or COOH;

$R_1$ is H, $C_1$–$C_6$ alkyl or $C_3$–$C_6$ cycloalkyl.

The invention is illustrated but not restricted to the following working examples.

WORKING EXAMPLES

Example 1

(R)-3-N,N-Dibenzylamino-5-methoxy-3,4-dihydro-2H-1-benzopyran (R)-3-Amino-5-methoxy-3,4-dihydro-2H-1-benzopyran (2.6 g, 14 mmol), $K_2CO_3$ (7.0 g, 51 mmol), benzylbromide (6.0 g, 35 mmol) and a catalytic amount of potassium iodide were mixed in acetonitrile (100 mL) under nitrogen. The reaction mixture was refluxed for 72 h. The solvent was removed in vacuo, and the residue was partitioned between diethyl ether and a 2 M $NH_3$ solution. The layers were separated, and the aqueous phase was extracted twice with diethyl ether. The ethereal layers were combined and dried ($MgSO_4$). The solvent was removed in vacuo to give a yellow oily residue which was purified by flash chromatography on silica gel (eluent: methylene chloride) affording 3.2 g (64% yield) of the title compound: EIMS (70 eV) m/z (relative intensity) 359 (91, $M^+$). The HCl salt was precipitated from diethyl ether at 0° C. and then recrystallized from ethanol/diethyl ether. The crystals were hygroscopic and started to melt at 100° C. and melted finally between 118 and 120° C.; $[\alpha]^{21}_D -20°$ (c 0.3, methanol).

Example 2

(S)-3-N,N-Dibenzylamino-5-methoxy-3,4-dihydro-2H-1-benzopyran

The title compound was synthesized according to the procedure described for its corresponding (R)-enantiomer: $[\alpha]^{21}_D$ (measured on the free base) +116° (c 1.0, chloroform).

Example 3

(R)-3-N,N-Dibenzylamino-5-hydroxy-3,4-dihydro-2H-1-benzopyran (R)-3-N,N-Dibenzylamino-5-methoxy-3,4-dihydro-2H-1-benzopyran hydrochloride (1.6 g, 4.0 mmol) was dissolved in methylene chloride (40 mL) under nitrogen, and the solution was cooled to −70° C. A solution of boron tribromide (1.8 g, 7.3 mmol) in methylene chloride (25 mL) was added dropwise over 5 min. The temperature was then allowed to slowly reach 0° C., and the reaction was stirred overnight. The reaction mixture was carefully poured into a saturated $NaHCO_3$ solution with stirring. The layers were separated and the aqueous phase was extracted three times with methylene chloride. The organic layers were combined and dried ($MgSO_4$). The solvent was removed in vacuo to give a brownish oily residue which was purified by flash chromatography on silica gel (eluent: methylene chloride) affording 0.14 g (98% yield) of the title compound: $[\alpha]^{21}_D -94°$ (c 0.1, methanol); EIMS (70 eV) m/z (relative intensity) 345 (100, $M^+$).

Example 4

(S)-3-N,N-Dibenzylamino-5-hydroxy-3,4-dihydro-2H-1-benzopyran

The title compound was synthesized according to the procedure described for its corresponding (R)-enantiomer. $[\alpha]^{21}_D +109°$ (c 1.0, chloroform).

Example 5

(R)-2-(3-N,N-Dibenzylamino-3,4-dihydro-2H-1-benzopyran-5-yloxy)-2-methylpropanamide (R)-3-N,N-Dibenzylamino-5-hydroxy-3,4-dihydro-2H-1-benzopyran (35.4 g, 100 mmol) was dissolved in anhydrous 1,4-dioxane (350 mL) under nitrogen. A dispersion of sodium hydride (60–65% in oil, 5.33 g, 130 mmol) was added in portions. The mixture was stirred for 2 h at room temperature. 2-Bromo-2-methylpropanamide (17.9 g, 110 mmol; described in Coutts, I. G. C.; Southcott, M. R. *J. Chem. Soc. Perkin Trans.* 1 1990, 767–771) was added to the dark greenish solution and was heated at reflux with stirring for 3 h. After cooling, a small amount of water was added, the solution was decanted, and the solvent was removed in vacuo. The residue was partitioned between ethyl acetate (350 mL) and a saturated $NaHCO_3$ solution (50 mL). The organic layer was dried ($MgSO_4$), and the solvent was removed in vacuo to give a brownish residue which was chromatographed on a short column of silica gel (eluent: hexane/ethyl acetate; 55:45) affording 27.6 g (64% yield) of the title compound as a white solid: mp 132–134° C.; $[\alpha]^{22}_D -92°$ (c 1.0, chloroform); EIMS (70 eV) m/z (relative intensity) 430 (6, $M_+$).

Example 6

(S)-2-(3-N,N-Dibenzylamino-3,4-dihydro-2H-1-benzopyran-5-yloxy)-2-methylpropanamide The title compound was synthesized according to the procedure described for its corresponding (R)-enantiomer: $[\alpha]^{21}_D +99°$ (c 1.0, chloroform).

Example 7

(R)-5-Amino-3-N,N-dibenzylamino-3,4-dihydro-2H-1-benzopyran 1,3-Dimethyl-3,4,5,6-tetrahydro-2(1H)-pyrimidinone (31 mL) was added to a stirred solution of (R)-2-(3-N,N-dibenzylamino-3,4-dihydro-2H-1-benzopyran-5-yloxy)-2-methylpropanamide (31.0 g, 72.0 mmol) in anhydrous N,N-dimethylformamide (310 mL) under nitrogen. Sodium hydride (60–65% in oil, 5.76 g, 144 mmol) was added in portions. The reaction mixture was heated at 100° C. and was stirred for 16 h. The mixture was then allowed to cool, and the solution was partitioned between ethyl acetate (500 mL) and a 2 M $NH_3$ solution (300 mL). The layers were separated, and the aqueous layer was extracted with ethyl acetate (150 mL). The combined organic layers were dried ($MgSO_4$) and concentrated in vacuo to give a brownish oil. The obtained material was dissolved in ethanol (400 mL). A 6 M HCl solution (500 mL) was added, and the reaction mixture was heated to reflux at 85° C. After stirring overnight, the mixture was allowed to cool to 35° C., the ethanolic solvent was concentrated in vacuo, and toluene was added to the residual aqueous solution. The mixture was cooled on ice, and a solution of conc. $NH_3$ was slowly added with stirring. An almost insoluble material formed. The alkaline two-phase system was transferred to a separatory funnel, and the insoluble material was treated with a 2 M $NH_3$ solution and ethyl acetate. Eventually, all material was dissolved and it was combined with the already obtained two-phase mixture. The layers were separated, and the aqueous layer was extracted with another portion of ethyl acetate. The combined organic layers were dried ($MgSO_4$), and the solvent was removed in vacuo to give a brownish oil which was purified on a short column of silica gel (eluent: hexane/ethyl acetate; 80:20) affording 19.0 g (72% yield) of the desired compound as a light yellow oil. The product slowly crystallized upon standing in the refrigerator: mp 99–101° C.; $[\alpha]^{21}_D -131°$ (c 1.0, chloroform); EIMS (70 eV) m/z (relative intensity) 344 (38, $M^+$).

Example 8

(S)-5-Amino-3-N,N-dibenzylamino-3,4-dihydro-2H-1-benzopyran

The title compound was synthesized according to the procedure described for its corresponding (R)-enantiomer:

[α]$^{21}_D$+123° (c 1.0, chloroform). An analytical sample was recrystallized from diethyl ether/petroleum ether: mp 101–103° C.

Example 9

(R)-3-N,N-Dibenzylamino-5-(4-methylpiperazin-1-yl)-3,4-dihydro-2H-1-benzopyran

To a solution of (R)-5-amino-3-N,N-dibenzylamino-3,4-dihydro-2H-1-benzopyran (2.86 g, 8.30 mmol) in a mixture of 15% water in acetonitrile (120 mL) were added sodium iodide (69 mg, 0.42 mmol) and N-methyl-bis(2-chloroethyl)amine hydrochloride (3.20 g, 16.6 mmol) with stirring. The clear solution was heated at reflux. After 7 h of stirring, NaHCO$_3$ (700 mg, 8.30 mmol) was added, and the reaction mixture was stirred for an additional 11 h. Another portion of NaHCO$_3$ (700 mg, 8.30 mmol) was added followed by continued reflux. After 6 h, a final portion of NaHCO$_3$ (350 mg, 4.15 mmol) was added, and the reaction mixture was stirred for 6 h more (30 h in all). The mixture was cooled on an ice-bath, and a 2 M NaOH solution (20 mL) was added with stirring. The two-phase system was stirred for 10 min after which the solvents were removed under reduced pressure until a precipitation occurred. The aqueous residue was extracted with diethyl ether (150 mL), the layers were separated, and the aqueous layer was extracted with diethyl ether (2×50 mL). The combined ethereal layers were dried (MgSO$_4$), and the solvent was removed in vacuo. The crude product was purified by column chromatography on silica (eluent: chloroform/ethanol; 95.5:4.5+0.5% conc. NH$_3$) affording 2.39 g (67% yield) of the title compound as a colorless oil: [α]$^{21}_D$−45° (c 1.0, chloroform); EIMS (70 eV) m/z (relative intensity) 427 (0.3, M$^+$).

Example 10

(S)-1-(3-N,N-Dibenzylamino-3,4-dihydro-2H-1-benzopyran-5-yl)-4-methylpiperazine-2,6-dione To a dispersion of N-methyliminodiacetic acid (6.90 g, 46.9 mmol) in anhydrous tetrahydrofuran (575 mL) was added 1,1'-carbonyldiimidazole (15.2 g, 93.9 mmol), and the mixture was heated at reflux for 2 h under nitrogen. A solution of (S)-5-amino-3-N,N-dibenzylamino-3,4-dihydro-2H-1-benzopyran (15.0 g, 42.7 mmol) in tetrahydrofuran (120 mL) was added with stirring over 0.5 h. The reaction mixture was heated at reflux for 28 h, then allowed to cool, and the solvent was removed in vacuo. The residue was purified on a short column of silica gel (eluent: methylene chloride and ethyl acetate) affording 14.1 g (71% yield) of the title compound as a light yellow solid: mp sinters>60° C.; [α]$^{21}_D$+89° (c 1.0, chloroform); EIMS (70 eV) m/z (relative intensity) 455 (8, M$^+$).

Example 11

(S)-3-N,N-Dibenzylamino-5-(4methylpiperazin-1yl)-3,4-dihydro-2H-1-benzopyran

To a stirred solution of (S)-1-(3-N,N-dibenzylamino-3,4-dihydro-2H-1-benzopyran-5-yl)-4-methylpiperazine-2,6-dione (25.4 g, 55.8 mmol) in anhydrous diethyl ether (800 mL) was added lithium aluminum hydride (9.30 g, 246 mmol) in portions. The reaction mixture was heated to reflux for 6.5 h under nitrogen and was stirred overnight at room temperature. The mixture was cooled (ice-bath), and water (10 mL) was added followed by a 15% aqueous solution of NaOH (10 mL) and another portion of water (30 mL). The precipitate was filtered off and washed with several portions of warm tetrahydrofuran. The organic layers were combined, and the solvent was removed in vacuo. The residue was purified by column chromatography on silica (eluent: chloroform/ethanol; 95:5+0.5% conc. NH$_3$) affording 13.6 g (57% yield) of the title compound as a light yellow oil: [α]$^{25}_D$+63° (c 1.0, methanol); EIMS (70 eV) m/z (relative intensity) 427 (5, M$^+$).

Example 12

(R)-3-Amino-5-(4-methylpiperazin-1-yl)-3,4-dihydro-2H-1-benzopyran

To a solution of (R)-3-N,N-dibenzylamino-5-(4-methylpiperazin-1-yl)-3,4-dihydro-2H-1-benzopyran (2.34 g, 5.47 mmol) in anhydrous methanol (100 mL) were added palladium (10%) on activated carbon (0.86 g) and ammonium formate (2.76 g, 43.8 mmol) under nitrogen. The reaction mixture was heated at 50° C. with stirring overnight. The solution was filtered through Celite®, and the solvent was removed in vacuo. The residue was partitioned between a 2 M NH$_3$ solution (20 mL) and ethyl acetate (100 mL). The layers were separated, and the aqueous layer was extracted with ethyl acetate (3×50 mL). The combined organic phases were dried (Na$_2$SO$_4$), and the solvent was removed in vacuo to give 1.21 g (90% yield) of the title compound as a pale yellow oil: [α]$^{21}_D$+15° (c 1.0, chloroform); EIMS (70 eV) m/z (relative intensity) 247 (6, M$^+$).

Example 13

(S)-3-Amino-5-(4-methylpiperazin-1-yl)-3,4-dihydro-2H-benzopyran

The title compound was synthesized according to the procedure described for its corresponding (R)-enantiomer: [α]$^{21}_D$−15° (c 1.0, chloroform).

Example 14

(S)-N-[5-(4-Methylpiperazin-1-yl)-3,4-dihydro-2H-1-benzopyran-3-yl]-4-morpholinobenzamide A solution of 4-morpholinobenzoic acid (380 mg, 1.83 mmol; described in: Degutis, J.; Rasteikiene, L.; Degutiene, A. Zh. Org. Khim. 1978, 14(10), 2060–2064) and 1,1'-carbonyldiimidazole (310 mg, 1.92 mmol) in anhydrous N,N-dimethylformamide (12 mL) was stirred at 75° C. for 30 min. The mixture was allowed to cool after which a solution of (S)-3-amino-5-(4-methylpiperazin-1-yl)-3,4-dihydro-2H-1-benzopyran (430 mg, 1.74 mmol) in N,N-dimethylformamide (8 mL) was added. The reaction mixture was stirred at room temperature for 3 days. Another portion of 1,1'-carbonyldiimidazole (57 mg, 0.35 mmol) was added, and the mixture was stirred for an additional 3.5 h. The solvent was removed in vacuo, and the residue was purified by column chromatography on silica (eluent: chloroform/ethanol; 93:7+0.5% NH$_3$) affording 513 mg (68% yield) of the title compound as a white solid: mp 210–212° C.; [α]$^{22}_D$−145° (c 1.0, chloroform); EIMS (70 eV) m/z (relative intensity) 436 (65, M$^{30}$).

Example 15

(R)-N-[5-(4-Methylpiperazin-1-yl)-3,4-dihydro-2H-1-benzopyran-3-yl]-4-morpholinobenzamide The title compound was synthesized according to the procedure described for its corresponding (S)-enantiomer: [α]$^{21}_D$+145° (c 1.0, chloroform).

Example 16

(S)-N-[5-(4-Methylpiperazin-1-yl)-3,4-dihydro-2H-1-benzopyran-3-yl]-4-piperidinobenzamide A suspension of 4-piperidinobenzoic acid (276 mg, 1.35 mmol; described in: Weringa, W. D.; Janssen, M. J. *Recl. Trav. Chim. Pays-Bas* 1968,87(12), 1372–1380) and 1,1'-carbonyldiimidazole (229 mg, 1.41 mmol) in anhydrous N,N-dimethylformamide (11 mL) was placed in an oil bath at 75° C. After 45 min of stirring, the mixture was allowed to cool. A solution of (S)-3-amino-5-(4-methylpiperazin-1-yl)-3,4-dihydro-2H-1-benzopyran (317 mg, 1.28 mmol) in N,N-dimethylformamide (5 mL) was added, and the mixture was stirred at room temperature for 40 h. Another portion of 1,1'-carbonyldiimidazole (83 mg, 0.51 mmol) was added, and the reaction was stirred for 3 days. At this time, the reaction was not complete and a final amount of 1,1'-carbonyldiimidazole (42 mg, 0.25 mmol) was added. The reaction mixture was heated for 3 h at 50° C. after which the solvent was removed in vacuo. The residue was purified by column chromatography on silica (eluent: chloroform/ethanol; 92:8+0.5% $NH_3$) affording 202 mg (36% yield) of the title compound as a white solid: mp 178–180° C.; $[\alpha]^{22}_D$–159° (c 1.0, chloroform); EIMS (70 eV) m/z (relative intensity) 434 (35, $M^{30}$).

Example 17

(S)-N-[5-(4-Methylpiperazin-1-yl)-3,4-dihydro-2H-1-benzopyran-3-yl]-4-butoxybenzamide A solution of 4-butoxybenzoic acid (650 mg, 3.35 mmol) in thionyl chloride (13 mL) was heated at 50° C. for 15 min after which the mixture was allowed to reach room temperature. The excess of thionyl chloride was removed under reduced pressure, and the residue was evaporated with two portions of toluene. The acid chloride was obtained as a brownish oil. A portion of the acid chloride (150 mg, 0.705 mmol) was dissolved in methylene chloride (5 mL) and added to an ice-cooled solution of (S)-3-amino-5-(4-methylpiperazin-1-yl)-3,4-dihydro-2H-1-benzopyran (159 mg, 0.643 mmol) and triethylamine (134 µL, 0.960 mmol) in anhydrous methylene chloride (20 mL). The ice-bath was removed, and the mixture was allowed to reach room temperature. The reaction mixture was washed with a saturated $NaHCO_3$ solution (10 mL), dried ($MgSO_4$), and the solvent was removed in vacuo. The residue was purified by column chromatography on silica (eluent: chloroform/ethanol; 92:8+0.5% conc. $NH_3$) affording 200 mg (74% yield) of the title compound as a white solid: mp 192–193.6° C.; $[\alpha]^{22}_D$–114° (c 1.0, chloroform); EIMS (70 eV) m/z (relative intensity) 423 (52, $M^{30}$).

Example 18

(R)-N-[5-(4-Methylpiperazin-1-yl)-3,4-dihydro-2H-1-benzopyran-3-yl]-4-butoxybenzamide The title compound was synthesized according to the procedure described for its corresponding (S)-enantiomer: $[\alpha]^{21}_D$+104° (c 1.0, chloroform).

Example 19

(S)-N-[5-(4-Methylpiperazin-1-yl)-3,4-dihydro-2H-1-benzopyran-3-yl]-4-trifluoromethylbenzamide A mixture of 4-trifluoromethylbenzoic acid (195 mg, 1.02 mmol) in thionyl chloride (5 mL) was heated at 50° C. for 20 min and then to reflux for 10 min. The mixture was allowed to cool after which the excess of thionyl chloride was removed in vacuo, and the residue was evaporated with two portions of toluene. The acid chloride was then dissolved in anhydrous methylene chloride (5 mL) and added to an ice-cooled solution of (S)-3-amino-5-(4-methylpiperazin-1-yl)-3,4-dihydro-2H-1-benzopyran (230 mg, 0.930 mmol) and triethylamine (194 µL, 1.39 mmol) in anhydrous methylene chloride (20 mL) with stirring. The reaction mixture was allowed to reach room temperature and was washed with a saturated $NaHCO_3$ solution. After drying ($MgSO_4$) and evaporation of the solvent in vacuo, a crude product was obtained which was purified by column chromatography on silica (eluent: chloroform/ethanol: 92:8+0.5% conc. $NH_3$). This procedure gave 214 mg (55% yield) of the title compound as a white solid: m p 212–214° C.; $[\alpha]^{22}_D$–73° (c 1.0, chloroform); EIMS (70 eV) m/z (relative intensity) 419 (100, $M^{30}$).

Example 20

(R)-N-[5-(4-Methylpiperazin-1-yl)-3,4-dihydro-2H-1-benzopyran-3-yl]-4-trifluoromethylbenzamide The title compound was synthesized according to the procedure described for its corresponding (S)-enantiomer: $[\alpha]^{21}_D$+74° (c 1.0, chloroform).

Example 21

(S)-N-[5-(4-Methylpiperazin-1-yl)-3,4-dihydro-2H-1-benzopyran-3-yl]-2,4-dimethoxybenzamide A solution of 2,4-dimethoxybenzoic acid (185 mg, 1.01 mmol) in thionyl chloride (5 mL) was heated at 55° C. for 15 min. The excess of thionyl chloride was removed in vacuo, and the residue was evaporated with two portions of toluene. The acid chloride was then dissolved in anhydrous methylene chloride (5 mL) and added to an ice-cooled solution of (S)-3-amino-5-(4-methylpiperazin-1-yl)-1,4-dihydro-2H-1-benzopyran (228 mg, 0.920 mmol) in anhydrous methylene chloride (20 mL) with stirring. The precipitated product was dissolved by the addition of triethylamine (193 µL, 1.38 mmol) to give a clear light yellow solution. The ice-bath was removed, and the reaction mixture was stirred at room temperature for 1 h. The mixture was washed with a saturated $NaHCO_3$ solution, dried ($MgSO_4$), and the solvent was removed in vacuo. The residue was purified by column chromatography on silica (eluent: chloroform/ethanol; 92.8+0.5% conc. $NH_3$) affording 268 mg (71% yield) of the title compound as an oil: $[\alpha]^{21}_D$–91° (c 1.0, chloroform); EIMS (70 eV) m/z (relative intensity) 411 (4, $M^{30}$). The base (238 mg, 0.578 mmol) was dissolved in anhydrous diethyl ether (10 mL) under nitrogen and was cooled on an ice-bath. A solution of HCl in diethyl ether (3 M, 0.5 mL), diluted with diethyl ether (5 mL), was added dropwise with stirring. The HCl salt was filtered, washed with diethyl ether, and dried in vacuo affording 187 mg (69% yield) of the product as a white powder: mp sinters>44° C.

Example 22

(S)-N-[5-(4-Methylpiperazin-1-yl)-3,4-dihydro-2H-1-benzopyran-3-yl]-4-N,N-diethylaminobenzamide A solution of 4-diethylaminobenzoic acid (189 mg, 0.978 mmol) and 1,1'-carbonyldiimidazole (166 mg, 1.02 mmol) in anhydrous N,N-dimethylformamide (5 mL) was stirred at 75° C. for 45 min. The mixture was allowed to cool, and a solution of (S)-3-amino-5-(4-methylpiperazin-1-yl)-3,4-dihydro-2H-1-benzopyran (230 mg, 0.930 mmol) in N,N-dimethylformamide (8 mL) was added. The reaction mixture was stirred at room temperature for 7 days. The solvent was removed in vacuo, and the residue was purified by column chromatography on silica (eluent: chloroform/ethanol; 92:8+0.5% $NH_3$) affording 234 mg (60% yield) of the title compound as a white solid: mp 218–219.6° C.; $[\alpha]^{21}_D$–178° (c 1.0, chloroform); EIMS (70 eV) m/z (relative intensity) 422 (29, $M^{30}$).

Example 23

(R)-N-[5-(4-Methylpiperazin-1-yl)-3,4-dihydro-2-1-benzopyran-3-yl]-4-N,N-diethylaminobenzamide The title compound was synthesized according to the procedure described for its corresponding (S)-enantiomer: $[\alpha]^{21}_D$+172° (c 1.0, chloroform).

Example 24

(S)-N-[5-(4-Methylpiperazin-1-yl)-3,4-dihydro-2H-1-benzopyran-3-yl]-furan-2-carboxamide To an ice-cooled stirred solution of (S)-3-amino-5-(4-methylpiperazin-1-yl)-3,4-dihydro-2H-1-benzopyran (230 mg, 0.930 mmol) and triethylamine (194 μL, 1.39 mmol) in anhydrous methylene chloride (10 mL) was added 2-furoyl chloride (101 μL, 1.02 mmol) under nitrogen. The ice-bath was removed, and the reaction mixture was allowed to reach room temperature. The mixture was washed with a 2 M $NH_3$ solution, dried ($MgSO_4$), and the solvent was removed in vacuo. The remains was purified on a chromatotron (accelerated thin layer chromatography, eluent: chloroform/ethanol; 92:8+0.5% conc. $NH_3$) affording 249 mg (79% yield) of the tile compound as a white solid; mp sinters>50° C.; $[\alpha]^{21}_D$–83° (c 1.0, chloroform); EIMS (70 eV) m/z (relative intensity) 341 (52, $M^{30}$).

Example 25

(S)-N-[5-(4-Methylpiperazin-1-yl)-3,4-dihydro-2H-1benzopyran-3-yl]-4-N,N-dimethylaminobenzamide A solution of 4-dimethylaminobenzoic acid (190 mg, 1.15 mmol) and 1,1'-carbonyldiimidazole (205 mg, 1.26 mmol) in anhydrous N,N-dimethylformamide (5 mL) was stirred at 75° C. for 35 min. The mixture was allowed to cool, and a solution of (S)-3-amino-5-(4-methylpiperazin-1-yl)-3,4-dihydro-2H-1-benzopyran (271 mg, 1.10 mmol) in N,N-dimethylformamide (5 mL) was added. The reaction mixture was stirred at room temperature for 4 days. The solvent was removed in vacuo, and the residue was purified by column chromatography on silica (eluent: chloroform/ethanol; 92:8+0.5% $NH_3$) affording 292 mg (67% yield) of the title compound as a white solid: mp 248–250°C; $[\alpha]^{21}_D$–175° (c 1.0, chloroform); EIMS (70 eV) m/z (relative intensity) 394 (467 $M^{30}$).

Example 26

(S)-N-[5-(4-Methylpiperazin-lyl)-3,4-dihydro-2H-1-benzopyran-3-yl]-pyrrole-2-carboxamide A mixture of 1,1'-carbonyldiimidazole (360 mg, 1.85 mmol) and pyrrole-2-carboxylic acid (225 mg, 2.03 mmol) in anhydrous N,N-dimethylformamide (8 mL) was stirred at 75° C. for 45 min. The mixture was allowed to cool, and a solution of (S)-3-amino-5-(4-methylpiperazin-1-yl)-3,4-dihydro-2H-1-benzopyran (457 mg, 1.85 mmol) in N,N-dimethylformamide (10 mL) was added. The reaction mixture was stirred for 7 days at room temperature under nitrogen. The solvent was removed in vacuo, and the residue was extracted with diethyl ether (50 mL) and water (20 mL). The aqueous layer was extracted with another portion of diethyl ether (50 mL). The combined ethereal layers were dried ($MgSO_4$), and the solvent was removed in vacuo. The residue was purified by column chromatography on silica (eluent: chloroform/ethanol; 90:10+0.5% conc. $NH_3$) yielding the title compound as an oil. Evaporation with diethyl ether afforded 300 mg (48% yield) of the title compound as a white powder: mp sinters>96° C.; $[\alpha]^{21}_D$–82.8° (c 1.0, chloroform); EIMS (70 eV) m/z (relative intensity) 340 (10, $M^{30}$).

Example 27

(S)-N-[5-(4-Methylpiperazin-1-yl)-3,4-dihydro-2H-1-benzopyran-3-yl]-5-methylpyridine-3-carboxamide A solution of 5-methylnicotinic acid (141 mg, 1.03 mmol) and 1,1'-carbonyldiimidazole (183 mg, 1.13 mmol) in anhydrous N,N-dimethylformamide (5 mL) was stirred at 75° C. for 55 min. The mixture was allowed to cool, and a solution of (S)-3-amino-5-(4-methylpiperazin-1-yl)-3,4-dihydro-2H-1-benzopyran (232 mg, 0.94 mmol) in N,N-dimethylformamide (5 mL) was added. The reaction mixture was stirred at room temperature for 28 h. The solvent was removed in vacuo, and the residue was purified by column chromatography on silica (eluent: chloroform/ethanol; 87:13+0.5% $NH_3$). The product was contaminated with a large amount of imidazole which could be removed by the following procedure: The mixture was dissolved in diethyl ether (100 mL), washed with water (2×20 mL) and treated with brine (10 mL). The ethereal layer was dried ($MgSO_4$), and the solvent was removed in vacuo to give 119 mg (35% yield) of the title compound as a white solid: mp sinters>68° C.; $[\alpha]^{21}_D$–82° (c 1.0, chloroform); EIMS (70 eV) m/z (relative intensity) 366 (21, $M^{30}$).

Example 28

(S)-N-[5-(4-Methylpiperazin-1-yl)-3,4-dihydro-2H-1-benzopyran-3-yl]-2,4-bis(trifluoromethyl)benzamide A solution of 2,4-bis(trifluoromethyl)benzoic acid (195 mg, 0.755 mmol) in thionyl chloride (4 mL) was heated at 55° C. for 45 min. The excess of thionyl chloride was removed in vacuo, and the residue was evaporated with two portions of toluene. The acid chloride wag then dissolved in anhydrous methylene chloride (5 mL) and added to a solution of (S)-3-amino-5-(4-methylpiperazin-1-yl)-3,4-dihydro-2H-1-benzopyran (170 mg, 0.687 mmol) and triethylamine (144 μL, 1.03 mmol) in anhydrous methylene chloride (20 mL) with stirring. The reaction mixture was left overnight at room temperature and was washed with a 2 M $NH_3$ solution (10 mL) followed by a portion of brine. The organic layer was dried ($MgSO_4$), and the solvent was removed in vacuo. The residue was purified by column chromatography on silica (eluent: chloroform/ethanol; 92:8+0.5% conc. $NH_3$) affording 100 mg (30% yield) of the title compound as a white powder: mp 202–203° C.; $[\alpha]^{21}_D$–51° (c 1.0, chloroform); EIMS (70 eV) m/z (relative intensity) 487 (16, $M^{30}$).

Example 29

(S)-N-[5-(4-Methylpiperazin-1-yl)-3,4-dihydro-2H-1-benzopyran-3-yl]-2-hydroxy-4-methoxybenzamide A solution of 4-methoxy-2-acetoxybenzoic acid (232 mg, 1.10 mmol; described in: Schonhofer, F. *Ber Deutsch Chem*

Ges 1951, 84, 13) in thionyl chloride (5 mL) was heated at 55° C. for 30 min. The excess of thionyl chloride was removed in vacuo, and the residue was evaporated with two portions of toluene. The acid chloride was then dissolved in anhydrous methylene chloride (5 mL) and added to a stirred solution of (S)-3-amino-5-(4-methylpiperazin-1-yl)-3,4-dihydro-2H-1-benzopyran (248 mg, 1.00 mmol) and triethylamine (210 μL, 1.50 mmol) in anhydrous methylene chloride (20 mL). The reaction mixture was stirred at room temperature for 2.5 h after which the mixture was washed with a saturated NaHCO$_3$ solution, dried (MgSO$_4$), and the solvent was removed in vacuo. The residue was dissolved in absolute ethanol (20 mL), and conc. NH$_3$ (5 mL) was added. The mixture was stirred overnight. The solvent was removed in vacuo, and the remains was purified by column chromatography on silica (eluent: chloroform/ethanol; 92:8+0.5% conc. NH$_3$) affording 120 mg (33% yield) of the title compound as a white solid: mp sinters>80° C.; $[\alpha]^{21}_D$ –92° (c 1.0, chloroform); EIMS (70 eV) m/z (relative intensity) 397 (27, M$^{30}$).

Example 30

(S)-N-[5-(4-Methylpiperazin-1-yl)-3,4-dihydro-2H-1-benzopyran-3-yl]-4-trifluoromethoxybenzamide A mixture of 4-trifluoromethoxybenzoic acid (254 mg, 1.23 mmol) in thionyl chloride (5 mL) was heated at 60° C. for 25 min. The excess of thionyl chloride was removed under reduced pressure, and the remains were evaporated with two portions of toluene. The acid chloride was then dissolved in anhydrous methylene chloride (5 mL) and added to a stirred solution of (S)-3-amino-5-(4-methylpiperazin-1-yl)-3,4-dihydro-2H-1-benzopyran (277 mg, 1.12 mmol) and triethylamine (234 μL, 1.68 mmol) in methylene chloride (10 mL). The reaction mixture was stirred for 2 h at room temperature and was washed with a saturated solution of NaHCO$_3$. The organic layer was dried (MgSO$_4$), and the solvent was removed in vacuo. The product was purified by column chromatography on silica (eluent: chloroform/ethanol, 92:8+0.5% conc. NH$_3$) affording 248 mg (51% yield) of the title compound as a white solid: mp 192–193° C.; $[\alpha]^{21}_D$ –75° (c 1.0, chloroform); EIMS (70 eV) m/z (relative intensity) 435 (6, M$^{30}$).

Example 31

4-(4-Piperidon-1-yl)benzoic Acid

A solution of 2 M NaOH (10 mL), 4-(8-aza-1,4-dioxaspiro[4,5]dec-8-yl)benzonitrile (820 mg, 3.36 mmol; described in: Taylor E. C.; Skotnicki J. S. Synthesis 1981, 8, 606–608), and ethanol (7.5 mL) was heated at reflux for 3 h. The external heating was interrupted, and the reaction mixture was stirred overnight at ambient temperature. The ethanolic solvent was removed in vacuo, and the remains were acidified to pH 4 with a 2 M HCl solution followed by extraction with ethyl acetate (50 ml). The layers were separated, and pH was adjusted to pH 6 with a 2 M NaOH solution followed by another extraction with ethyl acetate (50 mL). The combined organic layers were concentrated in vacuo, and the solid residue was dissolved in a 6 M HCl solution (10 mL). The reaction mixture was heated at 75° C. for 2.5 h and then at 55° C. overnight. The temperature was raised to 75° C. for 2 h, and the reaction mixture was then allowed to cool. The pH was adjusted to pH 4, and the solution was extracted with ethyl acetate (50 mL). The layers were separated, and another lo extraction was made at pH 5. The combined organic layers were dried (MgSO$_4$), and the solvent was removed in vacuo. The crude product was recrystallized from ethyl acetate affording 300 mg (41% yield) of the title compound as yellowish crystals: mp sinters>215° C.; EIMS (70 eV) m/z (relative intensity) 219 (100, M$^{30}$)

Example 32

(S)N[5-(4-Methylpiperazin-1-yl)-3,4-dihydro-2H-1-benzopyran-3-yl]-4-(4-piperidon-1-yl)benzamide A solution of 1,1'-carbonyldiimidazole (116 mg, 0.716 mmol) and 4-(4-piperidon-1-yl)benzoic acid (150 mg, 0.683 mmol) in anhydrous N,N-dimethylformamide (5 mL) was stirred at 75° C. for 50 min. The mixture was allowed to cool, and a solution of (S)-3-amino-5-(4-methylpiperazin-1-yl)-3,4-dihydro-2H-1-benzopyran (161 mg, 0.651 mmol) in N,N-dimethylformamide (4 mL) was added. The reaction mixture was stirred at room temperature for 8 days. The solvent was removed in vacuo, and the residue was purified by column chromatography on silica (eluent: chloroform/ethanol, 90:10+0.5% conc. NH$_3$) affording 54 mg (19% yield) of the title compound as a white solid: mp 222–225° C. (decomposes); $[\alpha]^{22}_D$ –136° (c 0.30, chloroform); TSPMS (70 eV) m/z 449 (M+1).

Example 33

(S)-N-[5-(4-Methylpiperazin-1-yl)-3,4-dihydro-2H-1-benzopyran-3-yl]-4-morpholinobenzenesulfonamide To a solution of (S)-3-amino-5-(4-methylpiperazin-1-yl)-3,4-dihydro-2H-1-benzopyran (120 mg, 0.485 mmol) in anhydrous methylene chloride (10 mL) were added triethylamine (81 μL, 0.582 mmol) and 4-(4-morpholinyl)benzenesulfonyl chloride (140 mg, 0.534 mmol; described in: Galliani, G. Eur. Pat. Appl. EP 335,758, 1989, Chem. Abstr. 1990, 112, 98374d [125393-22-8]). The reaction mixture was stirred at room temperature for 4 h, washed with a 2 M NH$_3$ solution, dried (MgSO$_4$) and concentrated in vacuo. The crude product was purified by column chromatography on silica (eluent: chloroform/ethanol, 90:10+0.5% conc. NH$_3$) affording 141 mg (61% yield) of the title compound as a white solid: mp sinters>100° C.; $[\alpha]^{22}_D$ +10° (c 1.0, chloroform); EIMS (70 eV) m/z (relative intensity) 472 (56, M$^{30}$).

Example 34

4-(Hexahydro-1,4-diazepin-5-on-1-yl)benzoic Acid

A solution of 4-(piperidon-1-yl)benzoic acid (281 mg, 1.28 mmol), conc. acetic acid (2 mL), and conc. H$_2$SO$_4$ (1 mL) was cooled to 5° C. Sodium azide (92 mg, 1.41 mmol) was added, and the reaction mixture was stirred at 7° C. for 42 h. A solution of 2 M NaOH was added to pH 5, and the resulting precipitate was filtered and washed with several portions of ice-cooled water. Drying in vacuo afforded 272 mg (91% yield) of the title compound as a white solid: mp 285–286° C.; EIMS (70 eV) m/z (relative intensity) 234 (66, M$^{30}$).

Example 35

(S)-N-[5-(4-Methylpiperazin-1-yl)-3,4-dihydro-2H-1-benzopyran-3-yl]-4-(hexahydro-1,4-diazepin-5-on-1-yl)benzamide A solution of 1,1'-carbonyldiimidazole (151 mg, 0.934 mmol) and 4-(hexahydro-1,4-diazepin-5-on-1-yl)benzoic acid (219 mg, 0.934 mmol) in anhydrous N,N-dimethylformamide (7 mL) was stirred at 75° C. for 55 min. The mixture was allowed to cool, and a solution of (S)-3-amino-5-(4-methylpiperazin-1-yl)-3,4-dihydro-2H-1-benzopyran (210 mg, 0.85 mmol) in N,N-dimethylformamide (3.5 mL) was added. The reaction mixture was stirred at room temperature for 14 days. The solvent was removed in vacuo, and the residue was purified by column chromatography on silica (eluent: chloroform/ethanol, 90:10+1% conc. $NH_3$). The product was crystallized from a mixture of chloroform, ethanol, and ethyl acetate affording 84 mg (21% yield) of the title compound as white crystals: mp 244–247° C. (decomposes); $[\alpha]^{21}_D$–148° (c 0.50, chloroform); TSPMS (70 eV) m/z 464 ($M^{30}$).

Example 36

(S)-N-[5-(4-Methylpiperazin-1-yl)-3,4-dihydro-2H-1-benzopyran-3-yl]-N'-(4-morpholino)phenyl Urea To a stirred solution of 4-morpholinobenzoic acid (126 mg, 0.606 mmol) and (S)-3-amino-5-(4-methylpiperazin-1-yl)-3,4-dihydro-2H-1-benzopyran (150 mg, 0.606 mmol) in acetonitrile (5 mL) was diphenylphosphoryl azide (131 μL, 0.606 mmol) added. The reaction mixture was heated at reflux for 1.5 h and was then allowed to cool to room temperature overnight. The solvent was removed in vacuo, and the residue was partitioned between ethyl acetate and a 2 M $NH_3$ solution. The organic layer was dried ($MgSO_4$), and the solvent was removed in vacuo. The residue was purified by column chromatography on silica (eluent: chloroform/ethanol, 90:10+0.5% conc. $NH_3$) affording 100 mg (36% yield) of the title compound as a white solid: mp sinters>118° C.; $[\alpha]^{21}_D$–71° (c 0.5, chloroform); MSTSP 452 (M+1).

Example 37

4-Bromo-3-methoxymorpholinobenzene

To a stirred slurry of 4-(3-methoxyphenyl)morpholine (1.54 g, 7.97 mmol; described in: Skowronska-Ptasinska M.; Verboon W.; Reinhoudt D. N. *J. Org. Chem.* 1985, 50(15), 2690–8) and sodium acetate (0.784 g, 9.56 mmol) in 1,4-dioxane (100 mL) was added a 0.25 M solution of bromine in 1,4-dioxane (35.0 mL, 8.77 mmol) over 45 min. Another portion of the bromine solution (15.0 mL, 4.00 mmol) and sodium acetate (0.523 g, 6.38 mmol) were added, and the reaction mixture was heated at 50° C. overnight. The solvent was removed in vacuo, and the residue was partitioned between diethyl ether (100 mL) and a 2 M $NH_3$ solution. The layers were separated, and the aqueous layer was extracted with diethyl ether (50 mL). The combined organic layers were dried ($MgSO_4$), and the solvent was removed in vacuo. The residue was filtered through a column of silica gel (eluent: chloroform/ethanol, 1:1+1.5% conc. $NH_3$), and the solvent was removed in vacuo. The residue was partitioned between methylene chloride and a 2 M $NH_3$ solution. After drying ($MgSO_4$) of the organic layer and removal of the solvent in vacuo, an orange oil was obtained which was purified by column chromatography on silica (eluent: methylene chloride+0.5% conc. $NH_3$) affording 450 mg (21% yield) of the title compound as a white solid: mp 103.5–104.5° C.; EIMS (70 eV) m/z (relative intensity) 273/271 (56/56, $M^{30}$).

Example 38

2-Methoxy-4-morpholinobenzoic Acid

To a stirred solution of 4-bromo-3-methoxy-1-morpholinobenzene (104 mg, 0.382 mmol) in anhydrous tetrahydrofuran (3 mL) at –78° C. was slowly added n-butyl lithium (1.3 M solution in hexanes, 325 μL, 0.420 mmol) under nitrogen. The cooling medium was exchanged with an ice-bath, and the mixture was stirred for 5 min. After cooling again to –78° C., carbon dioxide from evaporation of dry ice was bubbled through the solution for 10 min. A precipitate was formed, and the reaction mixture was allowed to reach room temperature. Diethyl ether and water were added. The mixture was extracted, the layers were separated, and the aqueous layer was acidified to pH 4. The dark blue aqueous solution was extracted several times with diethyl ether and ethyl acetate at pH 4 to pH 6. The combined organic layers were dried ($MgSO_4$), and the solvent was removed in vacuo affording 60 mg (66% yield) of the title compound as a white solid: mp 158–160° C.; EIMS m/z (relative intensity) 237 (100, $M^{30}$).

Example 39

(S)-[5-(4-Methylpiperazin-1-yl)-3,4-dihydro-2H-1-benzopyran-3-yl]-2-methoxy-4-morpholinobenzamide A stirred solution of 1,1'-carbonyldiimidazole (222 mg, 1.37 mmol) and 2-methoxy-4-morpholinobenzoic acid (176 mg, 0.740 mmol) in anhydrous N,N-dimethylformamide (5 mL) was heated at 75° C. for 2 h, and was then allowed to cool. A solution of (S)-3-amino-5-(4-methylpiperazin-1-yl)-3,4-dihydro-2H-1-benzopyran (183 mg, 0.740 mmol) in anhydrous N,N-dimethylformamide (4 mL) was added. The reaction mixture was stirred at room temperature for 5 days. The solvent was removed in vacuo, and the residue was partitioned between ethyl acetate (50 mL) and a 2 M $NH_3$ solution (15 mL). The organic layer was dried ($MgSO_4$), and the solvent was removed in vacuo. The residue was purified by column chromatography on silica (eluent: chloroform/ethanol, 93:7+0.5% conc. $NH_3$) affording 113 mg (30% yield) of the title compound as an uncolored foam: $[\alpha]^{21}_D$–141° (c 0.5, chloroform); EIMS (70 eV) m/z (relative intensity) 466 (20, $M^{30}$).

Example 40

4-(4-Benzylpiperazin-1-yl)benzonitrile

To a solution of 4-fluorobenzonitrile (3.0 g, 25 mmol) in N,N-dimethylformamide (15 mL) were added 1-benzylpiperazine (4.3 mL, 25 mmol) and potassium carbonate (3.4 g, 25 mmol). The reaction mixture was stirred at 120° C. for 13 h. The solvent was evaporated in vacuo and the residue was partitioned between ethyl acetate (100 mL) and water (15 mL). The aqueous phase was extracted with ethyl acetate (30 mL) and the combined organic phases were washed twice with brine (10 mL) and dried ($MgSO_4$). Evaporation of the solvent gave 7.6 g of crude product. Purification of the residue on a silica gel column using ethyl acetate/methylene chloride (1:9) as the eluent afforded 4.0 g (59% yield) of the title compound as a white solid: mp 104–105° C.; EIMS (70 eV) m/z (relative intensity) 277 (20, $M^{30}$).

Example 41

4-(4-Benzylpiperazin-1-yl)benzoic acid 4-(4-Benzylpiperazin-1-yl)benzonitrile (4.0 g, 15 mmol) was dissolved in glacial acetic acid (40 mL), 6 M hydrochloric acid (50 mL) was added and the reaction mixture was stirred at 100° C. for 17 h. The solvent was evaporated, the residue was suspended in water (10 mL) and the pH was adjusted to 3 by addition of 2 M sodium hydroxide (35 ml). The slurry was stirred at 50° C. for 2 h, cooled and the precipitate was filtered and dried in vacuo to give 4.1 g of a crude product. The solid was partitioned between methylene chloride (40 mL) and water (220 mL) with 2 M sodium hydroxide (8 mL). The aqueous phase wag washed with methylene chloride (40 mL) and the pH was adjusted to 5 with 2 M hydrochloric acid. The aqueous phase was cooled, the precipitate was filtered and dried in vacuo to give 1.6 g (38% yield) of the title compound: mp 226° C. (dec); EIMS (70 eV) m/z (relative intensity) 296 (44, $M^{30}$ ).

Example 42

(S)-N-[5-(4-Methylpiperazin-1-yl)-3,4-dihydro-2H-1-benzopyran-3-yl]-4-(4-benzylpiperazin-1-yl)benzamide A suspension of 4-(4-benzylpiperazin-1-yl)benzoic acid (1.3 g, 4.2 mmol) and 1,1'-carbonyldiimidazole (740 mg, 4.2 mmol) in N,N-dimethylformamide (30 mL) was heated to 75° C. for 1.5 h. The reaction mixture was cooled to 50° C. and a solution of (S)-3-amino-5-(4-methylpiperazin-1-yl)-3,4-dihydro-2H-1-benzopyran (1.0 g, 4.0 mmol) was added.

The solution was stirred at 50° C. for 20 h and the solvent was evaporated in vacuo giving 3.5 g of a crude product. Purification by chromatography on a silica gel column using chloroform/methanol/concentrated ammonia 95:5:0.5 as the eluent gave 1.7 g (80% yield) of the title compound as a pale yellow solid mp sinters>85° C.; TSPMS m/z (relative intensity) 526 (100, M+1); $[\alpha]^{22}_D$–13° (c 1.0, chloroform).

Example 43

(S)-N-[5-(4-Methylpiperazin-1-yl)-3,4-dihydro-2H-1-benzopyran-3-yl]-4-(piperazin-1-yl)benzamide (S)-N-[5-(4-Methylpiperazin-1-yl)-3,4-dihydro-2H-1-benzopyran-3-yl]-4-(4-benzylpiperazin-1-yl)benzamide (1.7 g, 3.2 mmol) was dissolved in methanol (100 mL). Palladium (10%) on activated carbon (510 mg) and ammonium formate (1.6 g, 26 mmol) were added and the reaction mixture was stirred at 50° C. for 19 h. The catalyst was filtered off and the solvent was evaporated in vacuo to give 1.3 g (92% yield) of the title compound as a pale yellow solid: mp>102° C. sinters; EIMS (70 eV) m/z (relative intensity) 435 (8, M⁺); $[\alpha]^{22}_D$–102° (c 0.15, chloroform).

Example 44

(S)-N-[5-(4-Methylpiperazin-1-yl)-3,4-dihydro-2H-1-benzopyran-3-yl]-4-(4-acetylpiperazin-1-yl)benzamide (S)-N-[5-(4-Methylpiperazin-1-yl)-3,4-dihydro-2H-1-benzopyran-3-yl]-4-(piperazin-1-yl)benzamide (460 mg, 1.0 mmol) was dissolved in N,N-dimethylformamide (5 mL) and acetyl chloride (82 μL, 1.2 mmol) was added.

The solution was stirred at ambient temperature for 1 h and the solvent was evaporated in vacuo. The residue was partitioned between methylene chloride (80 mL) and 2 M NaOH (10 mL). The organic layer was washed with brine (5 mL) and dried (MgSO₄). Evaporation of the solvent in vacuo gave 660 mg of a crude product. Purification by column chromatography on silica using chloroform/ethanol (saturated with ammonia) 15:1 as the eluent afforded 330 mg (66% yield) of the title compound as a white solid:mp 88° C. (dec); EIMS(70 eV) m/z (relative intensity) 477 (3, $M^{30}$ ), $[\alpha]^{22}_D$–138° (c 1.05, chloroform).

Example 45

(S)-N-[5-(4-Methylpiperazin-1-yl)-3,4-dihydro-2H-1-benzopyran-3-yl]-4-(morpholinocarbonyl)benzamide 4-(Morpholinocarbonyl)benzoic acid (100 mg, 0.43 mmol; described in: *J. Med. Chem.* 1994, 37(26), 4538–4554) and 1,1'-carbonyldiimidazole (76 mg, 0.47 mmol) were dissolved in N,N-dimethylformamide (3 mL) and heated to 75° C. for 3.5 h. Additional 1,1'-carbonyldiimidazole (36 mg, 0.22 mol) was added and the solution was stirred for 30 min. (S)-3-Amino-5-(4-methylpiperazin-1-yl)-3,4 dihydropyran-2H-1-benzopyran (100 mg, 0.40 mmol), dissolved in N,N-dimethylformamide (2 mL), was added and the reaction mixture was stirred for 18 h at 50° C. The solvent was evaporated and the residue was partitioned between ethyl acetate (30 mL) and water (5 mL). The organic layer was washed with water (5 mL) and brine (5 mL) and dried (MgSO₄). The solvent was evaporated in vacuo giving 180 mg of a crude product. Purification by preparative TLC twice using chloroform/methanol/concentrated ammonia 95:5:0.5 and chloroform/ethanol (saturated with NH₃) 12:1 as the eluents afforded 98 mg (53% yield) of the title compound as a white solid: mp 222° C. (decomposes); EIMS(70 eV) m/z (relative intensity) 464 (68, $M^{30}$ ); $[\alpha]^{22}_D$–12° (c 0.44, chloroform).

Example 46

(S)-N-[5-(4-Methylpiperazin-1-yl)-3,4-dihydro-2H-benzopyran-3-yl]-4-(N,N-dimethylaminocarbonyl)benzamide To 4-(N,N-dimethylaminocarbonyl)benzoic acid (110 mg, 0.56 mmol; described in: U.S. Pat. No. 3,607,918, 1971) was dropwise added thionyl chloride (500 μL, 6.9 mmol). The reaction mixture was stirred at ambient temperature for 1 min and then concentrated in vacuo. The excess of thionyl chloride was co-evaporated with toluene in vacuo. The crude acid chloride was dissolved in methylene chloride (8 mL) and dropwise added to a solution of (S)-3-amino-5-(4-methylpiperazin-1-yl)-3,4-dihydro-2H-1-benzopyran (130 mg, 0.53 mmol) and triethylamine (110 μL, 0.80 mmol in methylene chloride (5 mL) at 0° C. The reaction mixture was stirred at 0° C. for 30 min and at room temperature for an additional 30 min. The solvent was evaporated in vacuo giving 300 mg of a crude product. Purification by preparative TLC on silica using chloroform/ethanol (saturated with ammonia) 10:1 as the eluent afforded 120 mg (54% yield) of the title compound as a white solid: mp 219° C. (dec); EIMS (70 eV) m/z (relative intensity) 422 (47, $M^{30}$ ); $[\alpha]^{22}_D$–12° (c 0.42, chloroform)

Example 47

(S)-N-[5-(4-Methylpiperazin-1-yl)-3,4-dihydro-2H-1-benzopyran-3-yl]-4-[4-(2-benzyloxyethyl)-piperazin-1-yl]benzamide (S)-N-[5-(4-Methylpiperazin-1-yl)-3,4-dihydro-2H-1-benzopyran-3-yl]44piperazin-1-yl)benzamide (500 mg, 1.2 mmol) was dissolved in N,N-dimethylformamide (5 mL) and potassium carbonate (170 mg, 1.3 mmol) was added. To the mixture was added a solution of 2-benzyloxyethyl mesylate (290 mg, 1.3 mmol) (described in: Beard, C; Edwards, J; Fried, J. U.S Pat. No. 3,929,824, 1972 ) in N,N-dimethylformamide (5 mL). The reaction mixture was stirred at 40° C. for 24 h. The solvent was evaporated in vacuo giving 950 mg of a crude product. Purification by column chromatography on silica gel using chloroform/methanol/concentrated ammonia 95:5:0.5 as the eluent afforded 154 mg (24% yield) of the title compound as an oil: EIMS (70 eV) m/z (relative intensity) 569 (3, $M^{30}$).

Example 48

(S)-N-[5-(4-Methylpiperazin-1-yl)-3,4-dihydro-2H-1-benzopyran-3-yl]-4-[4-(2-hydroxyethyl)-piperazin-1-yl]benzamide (S)-N-[5-(4-Methylpiperazin-1-yl)-3,4-dihydro-2H-1-benzopyran-3-yl]-4-[4-(2-benzyloxyethyl)-piperazin-1-yl] benzamide (150 mg, 0.27 mmol) was dissolved in acetic acid (10 mL) and palladium (10%) on carbon (12 mg) was added. Hydrogenation at room temperature and at atmospheric pressure for 14 h followed by filtration and evaporation of the solvent in vacuo gave 180 mg of a crude product. The residue was partitioned between methylene chloride (60 mL) and 2 M $NH_3$ (5 mL) and washed with brine (5 mL). Drying ($MgSO_4$) the solution and evaporation of the solvent in vacuo gave 120 mg of crude material. Purification by preparative TLC on silica using chloroform/methanol/concentrated ammonia 95:5:0.5 as the eluent afforded 37 mg (29% yield) of the title compound as a white solid: mp 211–212° C.; EIMS (70 eV) m/z (relative intensity) 479 (8, $M^{30}$); $[\alpha]^{22}_D$ –26° (c 0.26, chloroform).

PHARMACOLOGY

Electrical Field Stimulation of [$^3$H]-5-HT Release from occipital Cortices of Guinea Pigs

[$^3$H]-5-HT is released by electrical field stimulation from slices of occipital cortices guinea pigs which have been pre-incubated with [$^3$H]-5-HT. This release is similar to that caused by nerve stimulation, i.e. exocytotic release from sertotoninergic nerve terminals, depending on the presence of $Ca^{2+}$ in the incubation medium. The 5-HT release is regulated at the level of the nerve terminals by autoreceptors, in the guinea pigs (like in humans) belonging to the h5-$HT_{1B}$ receptor subtype. Thus, agonists of h5-$HT_{1B}$ receptors reduce the amount of [$^3$H]-5-HT released by electrical field stimulation whereas the release is increased by antagonists of this receptor type. Testing compounds with this method is accordingly a convenient screening technique for determining the potency and functional effect of new h5-$HT_{1B}$ receptor agonists and antagonists.

METHODS AND MATERIALS

Buffer composition (mM) $NaHCO_3$ (25), $NaH_2PO_4 \cdot H_2O$ (1.2), NaCl (117), KCl(6), $MgSO_4 \times 7H_2O$(1.2), $CaCl_2$(1.3); EDTA $Na_2$(0.03). The buffer is gassed for at least 30 min before use. The pH of the buffer is about 7.2 in the room temperature but it rises to about 7.4 at 37° C.

Preparation of Occipital Cortical Slices

Guinea pigs (200–250 g) were decapitated and the whole brains were removed. The occipital cortices were dissected and cut to slices 0.4×4 mm with McIlwain chopper machine. The white part of the tissue should be removed carefully with a tweezer before slicing. The slices were incubated in 5 ml buffer in the presence of 5 mM pargyline chloride. After incubation with 0.1 mM [$^3$H]-5-HT for another 30 min the slices were transferred to a test tube and washed three times with same volume buffer. The slices were transferred to the superfusion chambers with a plastic pipette and were washed for 40 min with the buffer in the presence of uptake inhibitor citalopram 2.5 1M with a flow 0.5 ml/min.

Electrical Stimulation of 5-HT Release

The superfused buffer was collected in 2 mL/fraction. The slices were stimulated by electricity with a train of pulses of frequency 3 Hz, duration 2 ms and current 30 mA for 3 min at the 4th and 13th fractions. The tested drugs were added from the 8th fraction to the end of experiment.

RESULTS

A first electrical (or $K^+$) stimulation results in a standard amount of [$^3$H]5-HT released ($S_1$). Before the first and the second stimulation the h5-$HT_{1B}$ antagonist is added to the media which results in a dose dependent increase of the release ($S_2$) after the second stimulation. See FIG. 1.

The $S_2/S_1$, ratio which is the per cent of released [$^3$H]5-HT at the second stimulation ($S_2$) divided by that of the first stimulation ($S_1$), was used to estimate drug effects on transmitter release.

What is claimed is:

1. A compound of formula (I)

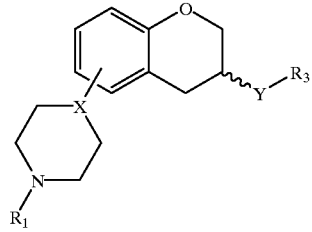

(I)

wherein
X is N;
Y is $CH_2NR_2$, $NR_2CO$, $CONR_2$, $NR_2SO_2$ or $NR_2CONR_2$ wherein $R_2$ is H or $C_1$–$C_6$ alkyl;
$R_1$ is H or $C_1$–$C_6$ alkyl;
$R_3$ is $(CH_2)_n$-phenyl,
    wherein the phenyl may be mono- or di-substituted with $R_4$ and/or $R_5$;
    wherein $R_4$ is selected from the group consisting of
    a) H,
    b) $C_1$–$C_6$ alkyl,
    c) $C_3$–$C_6$ cycloalkyl,
    d) halogen,
    e) CN,
    f) $CF_3$,
    g) OH,
    h) $C_1$–$C_6$ alkoxy,
    i) $NR_6R_7$,
    j) $OCF_3$,
    k) $SO_3CH_3$,
    l) $SO_3CF_3$,
    m) $SO_2NR_6R_7$,
    n) phenyl,
    o) phenyl-$C_1$–$C_6$ alkyl,
    p) phenoxy,
    q) $C_1$–$C_6$ alkylphenyl,
    r) an optionally substituted 5- or 6-membered heterocyclic ring containing one or two heteroatoms which is (are) N, wherein the substituent(s) is (are) selected from the group consisting of $C_1$–$C_6$ alkyl, $C_3$–$C_6$ cycloalkyl, phenyl-$C_1$–$C_6$ alkyl, $(CH_2)_mOR_9$ wherein m is 2–6 and $R_9$ is H, $C_1$–$C_6$ alkyl, $C_3$–$C_6$ cycloalkyl or phenyl-$C_1$–$C_6$ alkyl, and $COR_8$, s) an optionally substituted 5- or 6-membered heteroaromatic ring containing one or two heteroatoms which is (are) N, wherein the substituent(s) is (are) selected from the group consisting of $C_1-C_6$ alkyl, $C_3C_6$ cycloalkyl and phenyl-$C_1-C_6$ alkyl, and t) $COR_8$;

wherein $R_6$ is H, $C_1-C_6$ alkyl or $C_3-C_6$ cycloalkyl; $R_7$ is H, $C_1-C_6$ alkyl or $C_3-C_6$ cycloalkyl; and $R_8$ is $C_1-C_6$ alkyl, $C_3-C_6$ cycloalkyl, $CF_3$, $NR_6R_7$ or phenyl;

$R_5$ is selected from the group consisting of H, OH, $CF_3$, $OCF_3$, halogen, $C_1-C_6$ alkyl and $C_1-C_6$ alkoxy;

and n is 0–4;

wherein the compound is an (R)-enantiomer, an (S)-enantiomer, or a racemate in the form of a free base or a pharmaceutically acceptable salt or solvate thereof.

2. The compound according to claim 1 wherein Y is $NR_2CO$ or $CONR_2$.

3. The compound according to claim 1, wherein the phenyl ring of substituent $R_3$ is substituted with $R_4$, and $R_4$ is an optionally substituted 5- or 6-membered heterocyclic or heteroaromatic ring containing one or two heteroatoms which is (are) N; or $COR_8$.

4. The compound according to claim 1 or 3, wherein n is 0.

5. The compound according to claim 3 wherein $R_8$ is $NR_6R_7$.

6. The compound according to claim 2, wherein Y is $NR_2CO$.

7. The compound according to claim 1, wherein Y is $NR_2CO$ and $R_4$ is $COR_8$.

8. A compound selected from the group consisting of (S)-N-[5-(4-Methylpiperazin-1-yl)-3,4-dihydro-2H-1-benzopyran-3-yl]-4-piperidinobenzamide;

(S)-N-[5-(4-Methylpiperazin-1-yl)-3,4-dihydro-2H-1-benzopyran-3-yl]-4-butoxybenzamide;

(S)-N-[5-(4-Methylpiperazin-1-yl)-3,4-dihydro-2H-1-benzopyran-3-yl]4-trifluoromethylbenzamide;

(S)-N-[5-(4-Methylpiperazin-1-yl)-3,4-dihydro-2H-1-benzopyran-3-yl]-4-N,N-diethylaminobenzamide;

(S)-N-[5-(4-Methylpiperazin-1-yl)-3,4-dihydro-2H-1-benzopyran-3-yl]-4-trifluoromethoxybenzamide;

(S)-N-[5-(4-Methylpiperazin-1-yl)-3,4-dihydro-2H-1-benzopyran-3-yl]4-(4-piperidon-1-yl)benzamide; and (S)-N-[5-(4-Methylpiperazin-1-yl)-3,4-dihydro-2H-1-benzopyran-3-yl]-4-(4-benzylpiperazin-1-yl)benzamide in the form of a free base or a pharmaceutically acceptable salt or solvate thereof.

9. A pharmaceutical formulation comprising as active ingredient a therapeutically effective amount of the compound of claim 1 as an enantiomer or racemate, in the form of a free base or a pharmaceutically acceptable salt or solvate thereof optionally in association with diluents, excipients or inert carriers.

10. A method or the treatment of 5-hydroxytryptamine-mediated disorders, comprising administering to a patient in need of such treatment a therapeutically effective amount of the pharmaceutical formulation of claim 9.

11. A process for the preparation of the compound of formula I according to claim 1, comprising:

A(i)

acylation, in the case wherein $R_1$ is $C_1-C_6$ alkyl, Y is $NR_2CO$, $R_2$ is hydrogen and X and $R_3$ are as defined in claim 1, of a compound of formula A

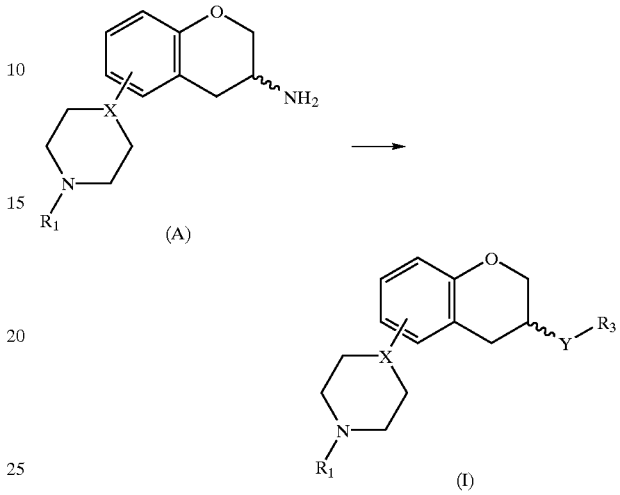

with an activated carboxylic acid $R_3$—$COLg_1$ wherein $Lg_1$ is a leaving group; or with a carboxylic acid $R_3$—COOH and an activating reagent; or A(ii)

acylation, in the case wherein $R_1$ is hydrogen, Y is $NR_2CO$, $R_2$ is hydrogen, $R_c$ is a protecting group and X and $R_3$ are as defined in claim 1, of a compound of formula B

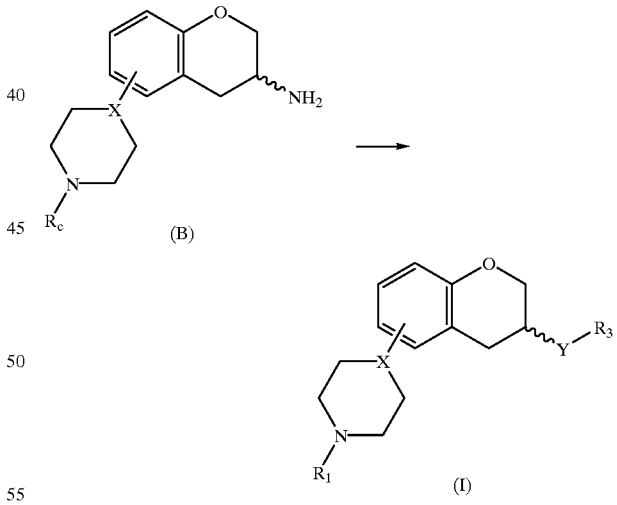

with an activated carboxylic acid $R_3$—$COLg_1$ wherein $Lg_1$ is a leaving group; or with a carboxylic acid $R_3$—COOH and an activating reagent, and removing the protecting group $R_c$.

* * * * *

UNITED STATES PATENT AND TRADEMARK OFFICE
CERTIFICATE OF CORRECTION

PATENT NO. : 6,479,497 B1 Page 1 of 1
DATED : November 12, 2002
INVENTOR(S) : Berg et al.

It is certified that error appears in the above-identified patent and that said Letters Patent is hereby corrected as shown below:

Column 7,
Line 44, delete "cod tain" and substitute therefor -- contain --.
Line 45, insert -- and -- between "saccharin" and "carboxymenthyl --.

Column 21,
Lines 55-64, that portion of the formula reading "$R_3$" should read -- $R_9$ --.

Column 40,
Line 10, delete "Before" and substitute therefor -- Between --.
Line 12, insert a hyphen between "dose" and "dependent".

Column 41,
Line 59, delete "or" and substitute therefor -- for --.

Signed and Sealed this

First Day of April, 2003

JAMES E. ROGAN
*Director of the United States Patent and Trademark Office*